US010101256B2

(12) United States Patent
Norisuye

(10) Patent No.: US 10,101,256 B2
(45) Date of Patent: Oct. 16, 2018

(54) ULTRASONIC PARTICLE SIZE MEASUREMENT DEVICE AND ULTRASONIC MEASUREMENT DEVICE

(71) Applicant: National University Corporation Kyoto Institute of Technology, Kyoto-shi, Kyoto (JP)

(72) Inventor: Tomohisa Norisuye, Kyoto (JP)

(73) Assignee: NATIONAL UNIVERSITY CORPORATION KYOTO INSTITUTE OF TECHNOLOGY, Kyoto (JP)

(*) Notice: Subject to any disclaimer, the term of this patent is extended or adjusted under 35 U.S.C. 154(b) by 0 days.

(21) Appl. No.: 15/549,734

(22) PCT Filed: Jan. 28, 2016

(86) PCT No.: PCT/JP2016/052511
§ 371 (c)(1),
(2) Date: Aug. 9, 2017

(87) PCT Pub. No.: WO2016/129399
PCT Pub. Date: Aug. 18, 2016

(65) Prior Publication Data
US 2018/0031464 A1 Feb. 1, 2018

(30) Foreign Application Priority Data

Feb. 12, 2015 (JP) .................................. 2015-025864
Feb. 12, 2015 (JP) .................................. 2015-025865

(51) Int. Cl.
*G01N 15/02* (2006.01)
*G01N 29/032* (2006.01)
(Continued)

(52) U.S. Cl.
CPC ......... *G01N 15/0211* (2013.01); *G01N 15/02* (2013.01); *G01N 29/024* (2013.01);
(Continued)

(58) Field of Classification Search
CPC .... G01N 15/0211; G01N 15/02; G01N 15/06; G01N 29/024; G01N 29/46;
(Continued)

(56) References Cited

U.S. PATENT DOCUMENTS 5,056,357 A  10/1991  Dymling et al.
5,121,629 A * 6/1992  Alba ..................... G01N 15/02
                                                           73/602
(Continued)

FOREIGN PATENT DOCUMENTS

JP      02-501956       6/1990
JP      2010-261910 A   11/2010
(Continued)

OTHER PUBLICATIONS

Berne,B.J.;Pecora,R.Dynamic Light Scattering with Applications to Chemistry,Biology and Physics;Dover Publications:Mineola,NY,2000.
(Continued)

*Primary Examiner* — Sang Nguyen
(74) *Attorney, Agent, or Firm* — Harness, Dickey & Pierce, P.L.C.

(57) ABSTRACT

An ultrasonic particle size measurement device includes: a transducer for (i) receiving an ultrasonic pulse scattered after being emitted to a fine particle and (ii) generating a first scattering amplitude Ψ; and a particle size calculating section for calculating a particle size of the fine particle by calculating an amplitude r and a phase θ in accordance with a real part and an imaginary part, respectively, of a second
(Continued)

scattering amplitude Ψ obtained by subjecting the first scattering amplitude Ψ to a Fourier transform.

13 Claims, 13 Drawing Sheets

(51) Int. Cl.
*G01N 29/46* (2006.01)
*G01N 29/24* (2006.01)
*G01N 29/024* (2006.01)

(52) U.S. Cl.
CPC ........... *G01N 29/032* (2013.01); *G01N 29/46* (2013.01); *G01N 2015/0216* (2013.01); *G01N 2015/0222* (2013.01); *G01N 2291/0289* (2013.01); *G01N 2291/02416* (2013.01)

(58) Field of Classification Search
CPC .............. G01N 29/348; G01N 29/032; G01N 2291/02416; G01N 2291/02809; G01N 2291/02818; G01N 2291/105; G01N 2015/0216; G01N 2015/0222
See application file for complete search history.

(56) References Cited

U.S. PATENT DOCUMENTS

| | | | | |
|---|---|---|---|---|
| 5,432,605 | A * | 7/1995 | Naqwi | G01B 11/105 356/485 |
| 5,569,844 | A * | 10/1996 | Sowerby | G01N 15/02 378/53 |
| 7,187,441 | B1 * | 3/2007 | Sevick-Muraca | G01N 15/0205 356/336 |
| 8,942,928 | B2 * | 1/2015 | Prakash | G01N 29/032 702/22 |
| 8,970,215 | B2 * | 3/2015 | Nieuwenhuis | B82Y 25/00 324/303 |
| 2006/0016498 | A1 * | 1/2006 | Takagi | B01J 8/0015 137/896 |
| 2008/0116056 | A1 * | 5/2008 | Folestad | G01N 22/04 204/157.15 |
| 2009/0158821 | A1 | 6/2009 | Sun et al. | |
| 2015/0260629 | A1 * | 9/2015 | Takeda | G01N 15/0255 356/72 |
| 2016/0123924 | A1 * | 5/2016 | Mason | G01N 27/44721 204/461 |

FOREIGN PATENT DOCUMENTS

| | | |
|---|---|---|
| JP | 2011-508208 A | 3/2011 |
| JP | 2013-108902 A | 6/2013 |

OTHER PUBLICATIONS

Cowan,M.L.;Page,J.H.;Weitz,D.A.Acoust.Imaging,26,247,2002.
Cowan,M.L.;Page,J.H.;Weitz,D.A.Phys,ReV.Lett.,85,453,2000.
M.Kohyama,T.Norisuye,and Q.Tran-Cong-Miyata,Polymer J.,40,5,pp. 398-399,2008.
T. Norisuye, et al., Development of a Novel Dynamic-Ultrasound Scattering technique for Characterization of Polymeric Materials. Sep. 4, 2007, vol. 56, No. 2, pp. 3600-3601 (1K19).
Kenta Igarashi, et al., Dynamics of submicron microsphere suspensions observed by dynamic ultrasound scattering techniques in the frequency-domain, Journal of Applied Physics 115, 203506 (2014).
Kohyama, Mariko et al., Dynamics of Microsphere Suspensions Probed by High Frequency Dynamic Ultrasound Scattering, Macromolecules, Jan. 13, 2009, vol. 42, pp. 752-759.
Nagao, Ayumi et al., Simultaneous Observation and Analysis of Sedimentation and Floating Motions of Microspheres Investigated by Phase mode-dynamic Ultrasound Scattering, Journal of Applied Physics, Jan. 30, 2009, vol. 105, pp. 23526-1~23526-7.
English Translation of International Preliminary Report on Patentability for PCT/JP2016/052511 dated Aug. 24, 2017.
International Search Report for PCT/JP2016/052511 dated Apr. 5, 2016.

* cited by examiner

ULTRASONIC PARTICLE SIZE MEASUREMENT DEVICE AND ULTRASONIC MEASUREMENT DEVICE

TECHNICAL FIELD

The present invention relates to an ultrasonic particle size measurement device for measuring, by use of an ultrasonic pulse, a particle size of fine particles (dispersoids) dispersed into a liquid (dispersion medium).

BACKGROUND ART

It is known that a diffusion constant and a hydrodynamic radius (particle size) of a fine particle having a particle size of approximately 1 nanometer (nm) to 3 micrometers (μm) can be quantified by a dynamic light scattering (DLS) method [Non-patent Literature 1]. In a case where laser light that is highly coherent is emitted to a solution sample obtained by dispersing particles into a solution, scattering of the laser light is observed depending on a size and a shape of the particles in the solution, and an intensity of the laser light changes over time in accordance with motion of the particles. In this case, it is empirically and theoretically clear that Brownian motion of a smaller particle can be seen as the intensity more rapidly declines over time in a time-intensity correlation function recorded in a photon correlator (correlator), whereas Brownian motion of a larger particle can be seen as the intensity more slowly declines over time in the time-intensity correlation function. As a result, motion and a particle size of a particle are analyzed through analysis of a relaxation time of a correlation function. Unlike, for example, an electron microscope, the dynamic light scattering method has an advantage of allowing an "as-is" state in which particles move in a solution (e.g., a state in which the particles swell, or a state in which the particles are weakly bound together) to be observed on a real-time basis. Note, however, that the dynamic light scattering method has the following problem. Specifically, according to the dynamic light scattering method, only a sample that is relatively transparent to laser light is analyzed, and it is difficult to carry out measurement with respect to a turbid sample, which is less light-transmissive.

In order to solve the problem, the inventors of the present invention have developed a dynamic ultrasound scattering (DSS) method in which attention is focused on similarity in wave between light and an ultrasonic wave. In the dynamic ultrasound scattering method, an ultrasonic wave that (i) is different from visible light in which a photon itself propagates through a space and (ii) is a wave in which a vibration is transmitted is used as a wave source. Thus, according to the dynamic ultrasound scattering method, difficulty in light transmission depending on, for example, whether a sample is colored or uncolored does not matter. The dynamic ultrasound scattering method was proposed by a Canadian group of John Page so that motion of a particle having a relatively large particle size of a millimeter to a submillimeter (approximately 1/10 of the millimeter) was studied [Non-patent Literature 2 and Non-patent Literature 3]. Page et al. used an ultrasonic wave of several megahertz (e.g., 2 MHz) to carry out complicated fluid analysis with respect to a fluidized bed and a Couette system. Thereafter, in order to apply the dynamic ultrasound scattering method not to analysis of a large particle as in the analysis carried out by Page et al., but to analysis of a smaller particle, the inventors of the present invention used an ultrasonic wave having a high frequency of 20 MHz to develop a "high frequency" dynamic ultrasound scattering method that is applicable to a fine particle having 3 micrometers to 32 micrometers As a result, validity of experimental results was shown by evaluating a sedimentation velocity of a fine particle and calculating a particle size in accordance with the evaluation [Non-patent Literature 4, Non-patent Literature 5, and Patent Literature 1]. Further, not only an average of velocities of sedimenting fine particles but also a change in velocity in accordance with a location of a particle and a time was quantified, and a relationship between (a) such a fluctuation in velocity and (b) a particle size was also analyzed by utilizing a hydrodynamic method [Non-patent Literature 5, Non-patent Literature 6, and Patent Literature 2].

In addition, a method for calculating a particle size of not only a sedimenting fine particle but also a fine particle in Brownian motion by use of a scattering amplitude of a real number which scattering amplitude is generated by an ultrasonic pulse is disclosed [Non-patent Literature 7].

CITATION LIST

Patent Literatures

[Patent Literature 1]
Japanese Patent Application Publication, Tokukai, No. 2010-261910 (Publication Date: Nov. 18, 2010)
[Patent Literature 2]
Japanese Patent Application Publication, Tokukai, No. 2013-108902 (Publication Date: Jun. 6, 2013)

Non-Patent Literatures

[Non-Patent Literature 1]
Berne, B. J.; Pecora, R. Dynamic Light Scattering with Applications to Chemistry, Biology and Physics; Dover Publications: Mineola, N.Y., 2000
[Non-Patent Literature 2]
Cowan, M. L.; Page, J. H.; Weitz, D. A. Acoust. Imaging, 26, 2 47, 2002
[Non-Patent Literature 3]
Cowan, M. L.; Page, J. H.; Weitz, D. A. Phys. ReV. Lett., 85, 45 3, 2000
[Non-Patent Literature 4]
M. Kohyama, T. Norisuye, and Q. Tran-Cong-Miyata, Polymer J., 40, 5, pp. 398-399, 2008
[Non-Patent Literature 5]
M. Kohyama, T. Norisuye, and Q. Tran-Cong-Miyata, Macromolecules, 42, 3, pp. 752-759, 2009
[Non-Patent Literature 6]
A. Nagao, M. Kohyama, T. Norisuye, and Q. Tran-Cong-Miyata, Journal of Applied Physics, 105, 023526, 2009
[Non-Patent Literature 7]
K. Igarashi, T. Norisuye, K. Kobayashi, K. Sugita, H. Nakanishi, and Q. Tran-Cong-Miyata, 115, 203506 (2014).

SUMMARY OF INVENTION

Technical Problem

Brownian motion of fine particles having been dispersed into a liquid and having a particle size in an order of nanometers is observed by the dynamic light scattering method (described earlier) substantially irrespective of a density of the particles, and a particle size d can be found based on Stokes-Einstein's equation expressed by Equation (1).

[Math. 1]

$$d = \frac{kT}{3\pi\eta D}$$ Equation (1)

Note here that in Equation (1), d is a diameter of a fine particle, which is a dispersoid, k is Boltzmann constant, T is an absolute temperature, π is a ratio of the circumference of a circle to its diameter, η is a viscosity of a dispersion medium, and D is a diffusion coefficient of the fine particle.

In a case where the particle has a particle size as large as a micrometer (micron) size, an influence of a self weight of the particle cannot be ignored, so that sedimentation motion is more dominant than Brownian motion, and the particle size d can be found based on Stokes' equation expressed by Equation (2).

[Math. 2]

$$\frac{4}{3}\pi\left(\frac{d}{2}\right)^3 \Delta\rho g = 6\pi\eta\frac{d}{2}V_0, \quad d = \sqrt{\frac{18\eta V_0}{\Delta\rho g}}$$ Equation (2)

Note here that in Equation (2), Δρ is a difference in density between the fine particle (dispersoid) and the dispersion medium, g is a gravitational acceleration, and $V_0$ is a terminal velocity of the fine particle during sedimentation.

A contribution of Brownian motion and sedimentation motion to the particle size d is discriminated by use of a character, which is Peclet number (a dimensionless number indicative of a ratio between advection and diffusion). A state of sedimentation motion can be examined by use of the dynamic ultrasound scattering method (DSS, Non-patent Literature 5), which was previously proposed by the inventors of the present invention. For measurement with respect to a particle having a micron size that exceeds a wavelength of light, the dynamic ultrasound scattering method is suitable in terms of a relationship between (a) a size of a particle, which is an object to be detected, and (b) a wavelength. Typically, the dynamic ultrasound scattering method makes it possible to analyze a particle size of approximately several micrometers to several ten micrometers.

Note, however, that a particle size analyzed by a conventional dynamic ultrasound scattering method (Non-patent Literature 5) has an analytical error of as high as approximately 10%, and a method for analyzing a particle size with high accuracy is desired. A first object to be attained by the present invention is to analyze a particle size of a fine particle with higher accuracy.

FIG. 16 is a view for explaining a method in which a particle size of a fine particle in a solution is measured by a dynamic ultrasound scattering method (DSS). The dynamic ultrasound scattering method is a method of nondestructive and non-contact evaluation of a state of motion, a structure, and a particle size of a fine particle 103 in a suspended solution 102. The particle size of the fine particle 103 can be obtained in a case where an ultrasonic beam 104 is emitted to the suspended solution 102 (fine particle solution) which has been poured into a cell 105, a scattered wave of the ultrasonic beam 104 is received by a single ultrasonic sensor 101 or different ultrasonic sensors 101 (transducer (s), a single ultrasonic sensor is used in FIG. 16), and a sedimentation velocity and a diffusion coefficient each shown in FIG. 16 are measured.

FIG. 17 is a view for explaining a relationship between (a) a change over time in scattered wave and (b) a change in location of a fine particle, which change is caused by motion of the fine particle, in the method in which a particle size is measured by the dynamic ultrasound scattering method. The scattered wave changes in intensity every moment in accordance with the state of motion of the fine particle. Since a change (displacement) of coordinates of the fine particle is understood from (i) a signal at a certain time T and (ii) a scattered wave signal at a time (T+τ) after the elapse of a given time τ from the time T, a quantitative velocity and a diffusion coefficient of the fine particle can be statistically calculated from the change (displacement) of the coordinates of the fine particle.

Effectiveness of the dynamic ultrasound scattering method has been shown against a sample with respect to which it is difficult to carry out measurement by use of light. Examples of the effectiveness include calculation, without dilution of a sample, of a sedimentation velocity and a particle size of a fine particle contained in a high concentration emulsion and having approximately several μm to several ten μm. For example, since a structure in an aggregational state disappears by dilution, it is preferable to actually measure an undiluted solution in an aggregational state. The dynamic ultrasound scattering method is favorable for measurement to be carried out with respect to a structure that is in an aggregational state and cannot be subjected to measurement by use of an electron microscope. A deviation from an average velocity is referred to as a fluctuation in velocity (standard deviation). Unlike measurement (state understanding) of a terminal velocity, which measurement has been known for a long time, accurate measurement (state understanding) of a fluctuation in sedimentation velocity of a fine particle is an extremely difficult problem and a research challenge to which an interest is still drawn in the field of a complex fluid.

It is known that fine particles in the fluctuation in velocity, which particles each have a size of several μm, are in motion in a mass of enormous fine particles at a millimeter level. Note, however, that such mass motion of the fine particles can be visualized without scanning of an ultrasonic beam in a case where the dynamic ultrasound scattering method (DSS) is used in combination. As an ultrasonic sensor to be used in an experiment, a broadband transducer capable of emitting a broadband ultrasonic wave having a frequency of 5 MHz to 20 MHz is frequently used. Due to (i) an ultrasonic sensor having a higher frequency of 30 MHz and (ii) review of a measurement and analysis system, such a broadband transducer has recently dramatically improved in resolving power at which to carry out measurement. This makes it possible to measure a particle size of a fine particle having a hydrodynamic radius of up to 100 nm. Such particle size measurement is a result obtained by grasping Brownian motion, which is a characteristic of a submicron fine particle, while using an ultrasonic wave whose wavelength is greater than that of light. The particle size measurement has been achieved because it was possible to (i) record a diffusion mode serving as a proof of the Brownian motion and (ii) evaluate a quantitative diffusion coefficient.

The conventional dynamic ultrasound scattering method (DSS method) thus makes it possible to measure a state of motion and a particle size of a highly suspended fine particle. Note, however, the following problems still remain to be solved.

According to the conventional dynamic ultrasound scattering method, an ultrasonic wave that is also generally usable to, for example, nondestructive testing or the medical field in general and has sufficiently small energy is used as an illumination source. This is because the following problem arises. Specifically, since a significant increase in applied effective energy of an ultrasonic wave causes a fine particle to be in motion due to ultrasonic energy itself applied to observe the fine particle, motion of the fine particle may be overestimated. That is, in a case where motion of a fine particle is desired to be observed as it is, especially energy of an ultrasonic wave is reduced.

Note, however, that an excessive reduction in applied effective energy of an ultrasonic wave causes a problem such that a scattered wave from a fine particle also has a lower intensity, and a difference between the intensity of the scattered wave and noise is narrowed, so that a signal-to-noise (hereinafter abbreviated to "SN") ratio deteriorates, and a particle velocity, a particle size, and the like cannot be accurately measured. Measurement accuracy is desired to be improved by a method in which ultrasonic energy can be positively utilized without concern for a problem of applied energy of an ultrasonic wave.

Further, according to the conventional dynamic ultrasound scattering method, an ultrasonic wave whose energy level is reduced as much as possible is emitted to a fine particle so that a state of the fine particle is analyzed in accordance with a natural sedimentation velocity and a diffusion coefficient of the fine particle. A sample of a fine particle whose sedimentation velocity and diffusion coefficient are extremely low causes the following problem. Specifically, such a fine particle has an extremely low motion velocity, and it takes much time to carry out measurement with respect to the fine particle. For example, measurement with respect to a fine particle of approximately 3 µm may require a waiting time that is approximately not less than 20 minutes. In particular, in a case where a dispersion medium has a high viscosity, a fine particle to be subjected to measurement substantially stands still without sedimenting. This causes a serious problem of an impossibility of obtaining effective measurement data. A second object to be attained by the present invention is to (i) limit ultrasonic wave applied energy that causes a deterioration in SN ratio of a scattered wave from a fine particle and (ii) shorten much measurement time required for measurement of a particle size of a fine particle having an extremely low motion velocity.

The present invention has a first object to provide an ultrasonic particle size measurement device that allows a particle size of a fine particle that is in relatively rapid motion to be measured at a high SN ratio and with high accuracy.

The present invention has a second object to provide an ultrasonic particle size measurement device that allows a particle size of a fine particle that is in slow motion to be measured at a favorable SN ratio and in a short time.

Solution to Problem

In order to attain the first object, an ultrasonic particle size measurement device in accordance with an embodiment of the present invention includes: an ultrasonic wave receiver for (i) receiving an ultrasonic pulse scattered after being emitted to a fine particle sedimenting in a liquid and (ii) generating a first scattering amplitude $\Psi$ (t,T) based on a propagation time t of the ultrasonic pulse and an observation time T with respect to motion of the fine particle; and a particle size calculating section for (i) generating a second scattering amplitude $\Psi$ (f,T) obtained by subjecting the first scattering amplitude $\Psi$ (t,T) to a Fourier transform in a direction of the propagation time t, (ii) calculating an amplitude r (f,T) and a phase $\theta$ (f,T) in accordance with a real part and an imaginary part, respectively, of the second scattering amplitude $\Psi$ (f,T), and (iii) calculating a particle size of the fine particle in accordance with the amplitude r (f,T) and the phase $\theta$ (f,T).

In order to attain the second object, an ultrasonic particle size measurement device in accordance with an embodiment of the present invention includes: an ultrasonic energy applicator for applying ultrasonic energy to a fine particle so as to induce an ultrasonic fine particle velocity in the fine particle; a scattered wave receiver for receiving a scattered wave scattered by the fine particle in which the ultrasonic fine particle velocity has been induced; an ultrasonic fine particle velocity calculating section for calculating the ultrasonic fine particle velocity in accordance with the scattered wave received by the scattered wave receiver; and a particle size calculating section for calculating a particle size of the fine particle in accordance with the ultrasonic fine particle velocity calculated by the ultrasonic fine particle velocity calculating section.

An ultrasonic measurement apparatus in accordance with an embodiment of the present invention includes: a first ultrasonic particle size measurement device in accordance with an embodiment of the present invention; and a second ultrasonic particle size measurement device in accordance with an embodiment of the present invention.

Advantageous Effects of Invention

According to an ultrasonic particle size measurement device in accordance with an embodiment of the present invention, an amplitude r (f,T) and a phase $\theta$ (f,T) of a second scattering amplitude $\Psi$ (f,T) are calculated in accordance with a real part and an imaginary part, respectively, of the second scattering amplitude $\Psi$ (f,T) obtained by subjecting a first scattering amplitude $\Psi$ (t,T) to a Fourier transform in a direction of a propagation time t, and a particle size of a fine particle is calculated in accordance with the amplitude r (f,T) and the phase $\theta$ (f,T). Thus, the ultrasonic particle size measurement device in accordance with an embodiment of the present invention yields a first effect of measuring, at a high SN ratio and with extremely high accuracy, a particle size of a fine particle that is in relatively rapid motion.

According to an ultrasonic particle size measurement device in accordance with an embodiment of the present invention, a fine particle velocity influenced by an ultrasonic wave (this is referred to as an "ultrasonic fine particle velocity") is actively induced in a fine particle by applying, to the fine particle, ultrasonic energy that is energy at a level equal to or higher than a level that influences motion of the fine particle, and the ultrasonic fine particle velocity is calculated in accordance with a scattered wave scattered by the fine particle in which the ultrasonic fine particle velocity has been induced. Thus, the ultrasonic particle size measurement device in accordance with an embodiment of the present invention yields a second effect of (i) achieving a favorable SN ratio and (ii) measuring, in a short time, a particle size of a fine particle that varies in solvent and/or particle size and is in slow motion in many cases.

Figure 2:
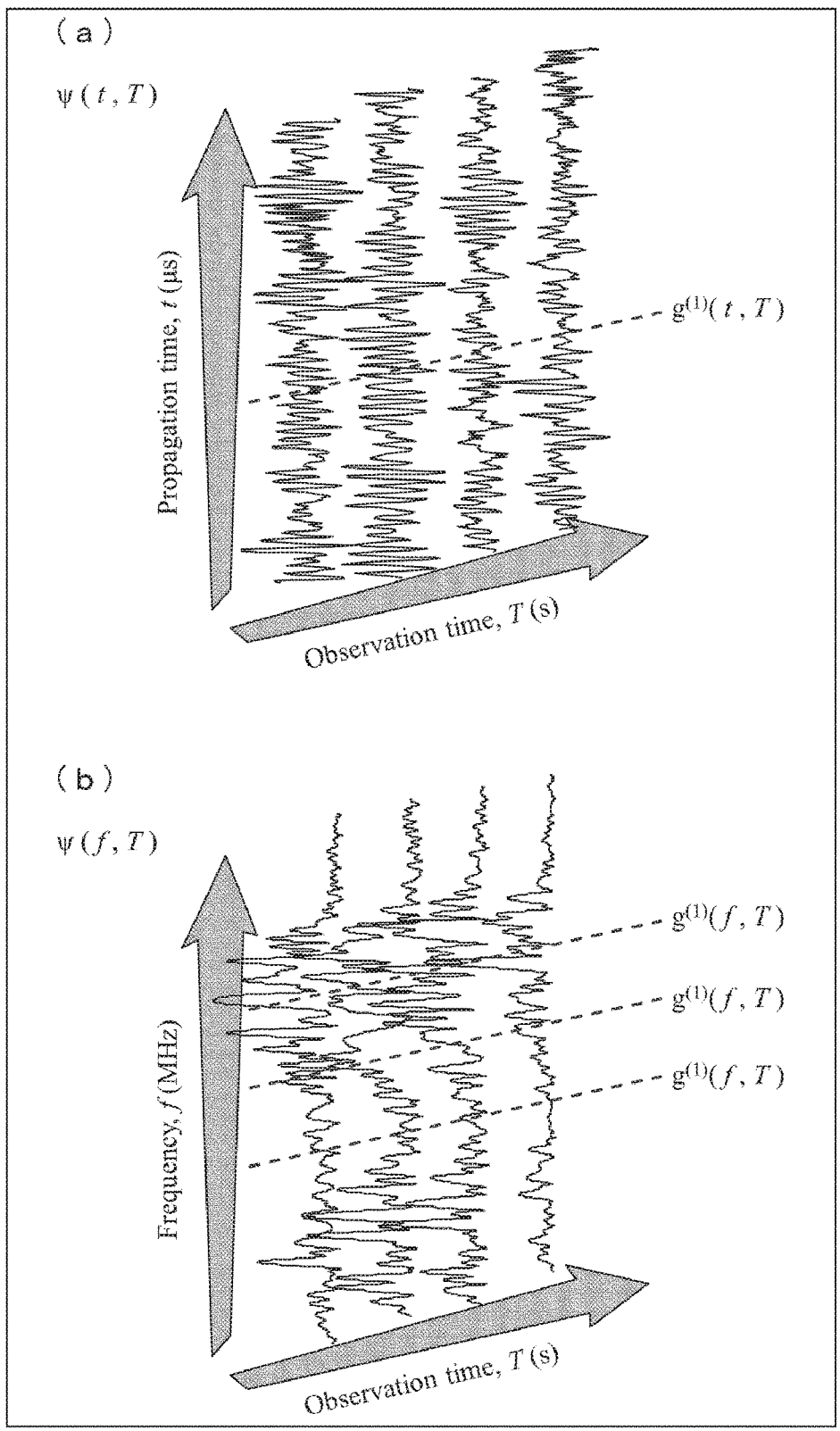

(a) of FIG. 2 shows a graph schematically indicating a first scattering amplitude Ψ (t,T) measured by use of the ultrasonic particle size measurement device. (b) of FIG. 2 shows a graph schematically indicating a second scattering amplitude (f,T) measured by use of the ultrasonic particle size measurement device.

Figure 3:
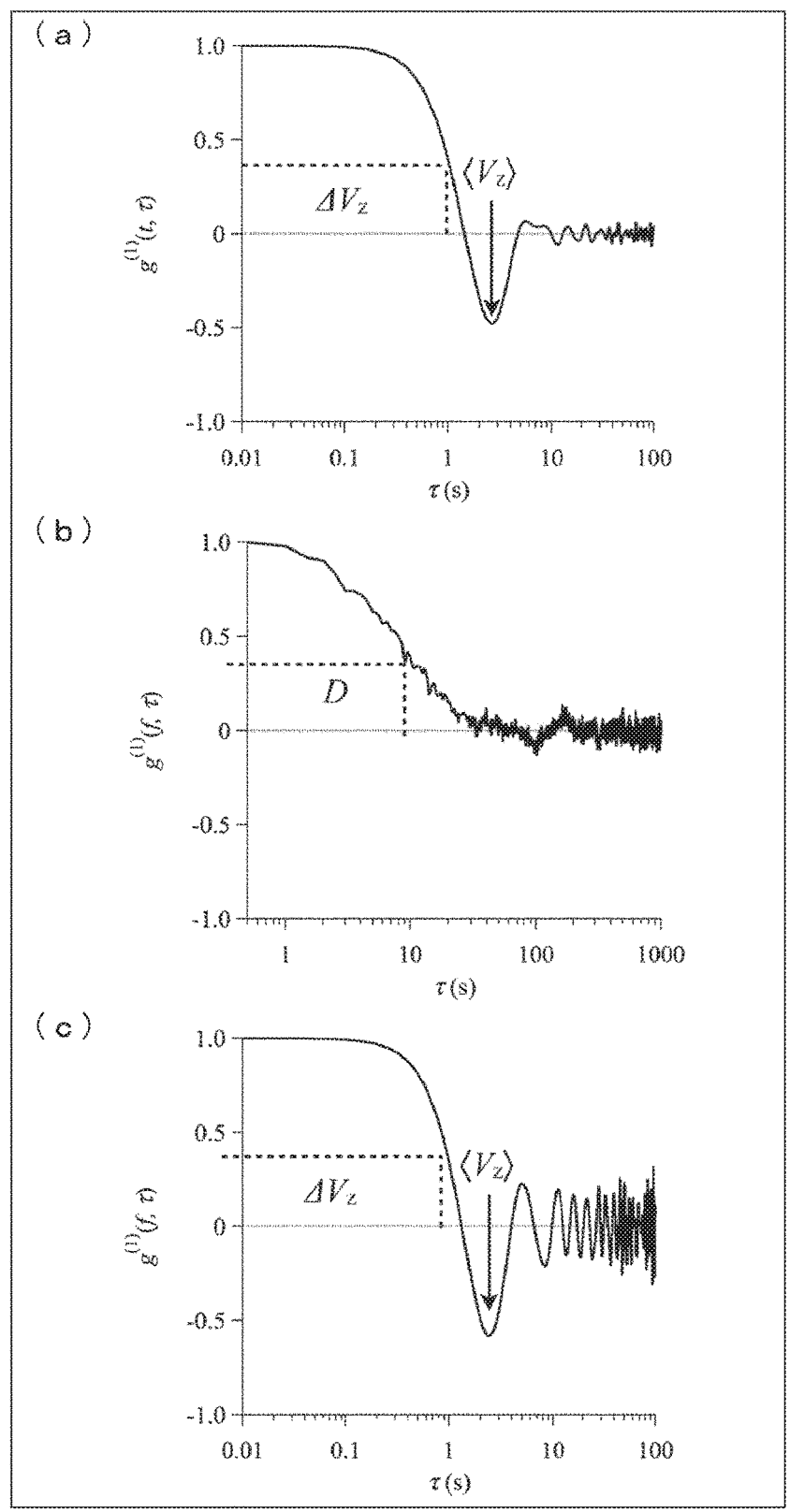

(a) of FIG. 3 shows a graph indicating a correlation function obtained by a time domain correlation function method. (b) of FIG. 3 shows a graph indicating a correlation function obtained by a method in which calculation is carried out in view of a real part of a scattering amplitude influenced by an ultrasonic pulse. (c) of FIG. 3 shows a graph indicating a correlation function measured by use of the ultrasonic particle size measurement device.

Figure 4:
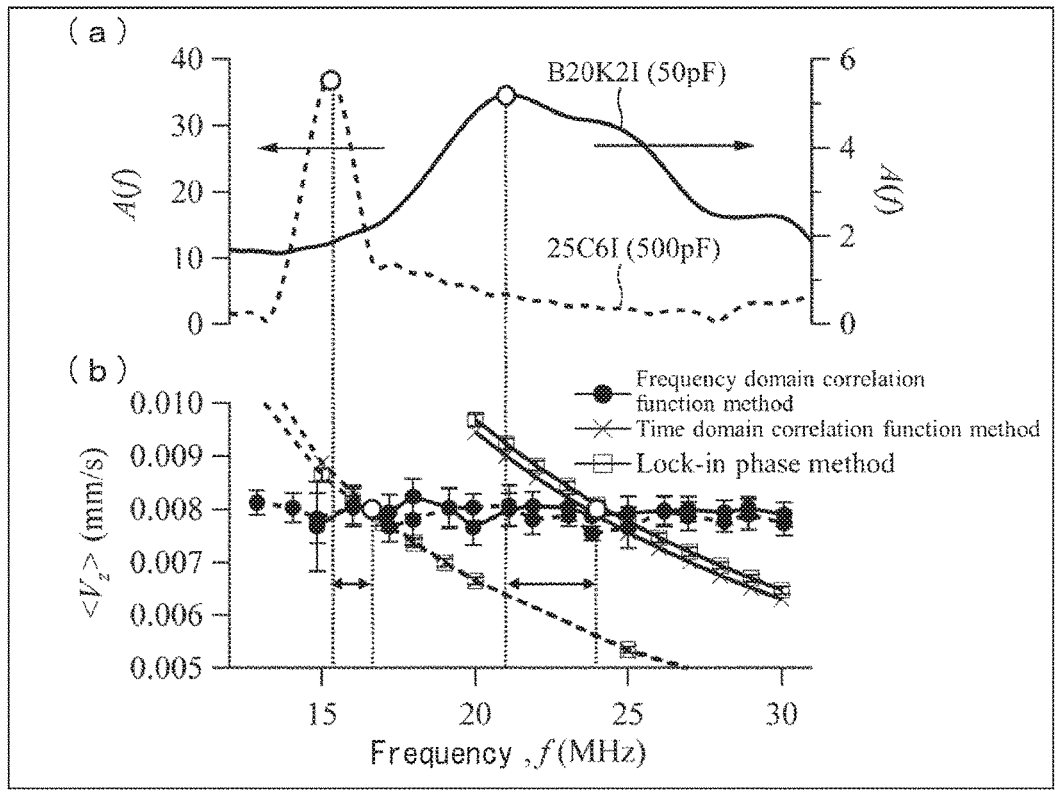

(a) and (b) of FIG. 4 show graphs each indicating a result of measurement, by the ultrasonic particle size measurement device, of a sedimentation velocity of polymer particles dispersed into water.

Figure 5:
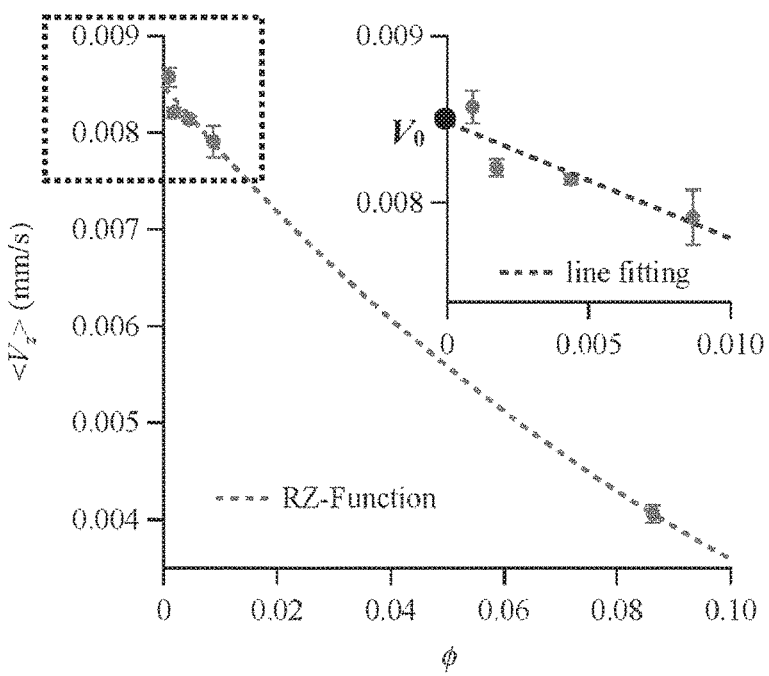

FIG. 5 shows a graph indicating particle concentration dependence of a sedimentation velocity analyzed by use of a lock-in phase method calibrated by a method in accordance with Embodiment 1.

Figure 6:
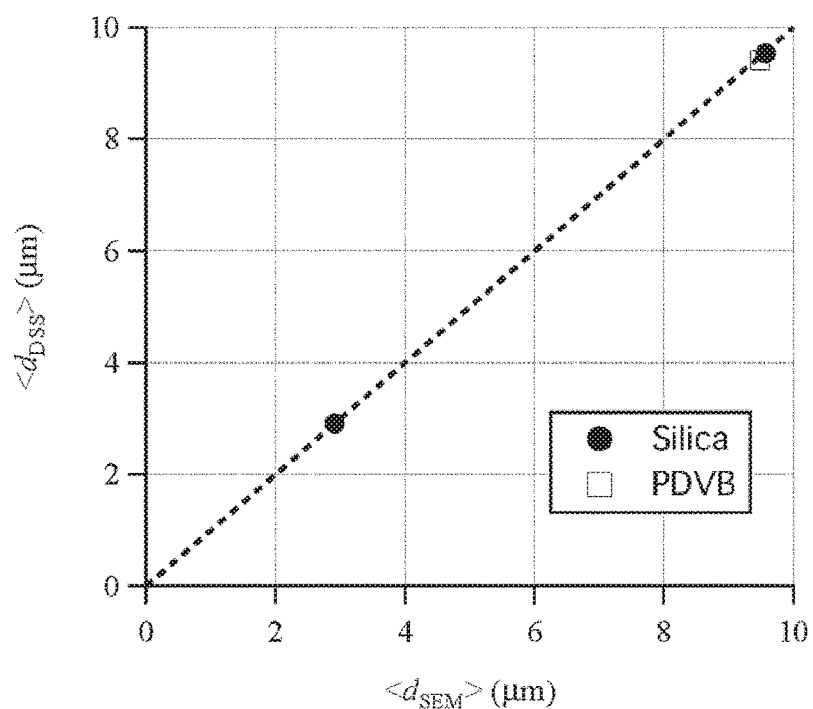

FIG. 6 shows a graph indicating a relationship between (a) a particle size measured by use of the ultrasonic particle size measurement device and (b) a particle size measured by use of a scanning electron microscope.

Figure 7:
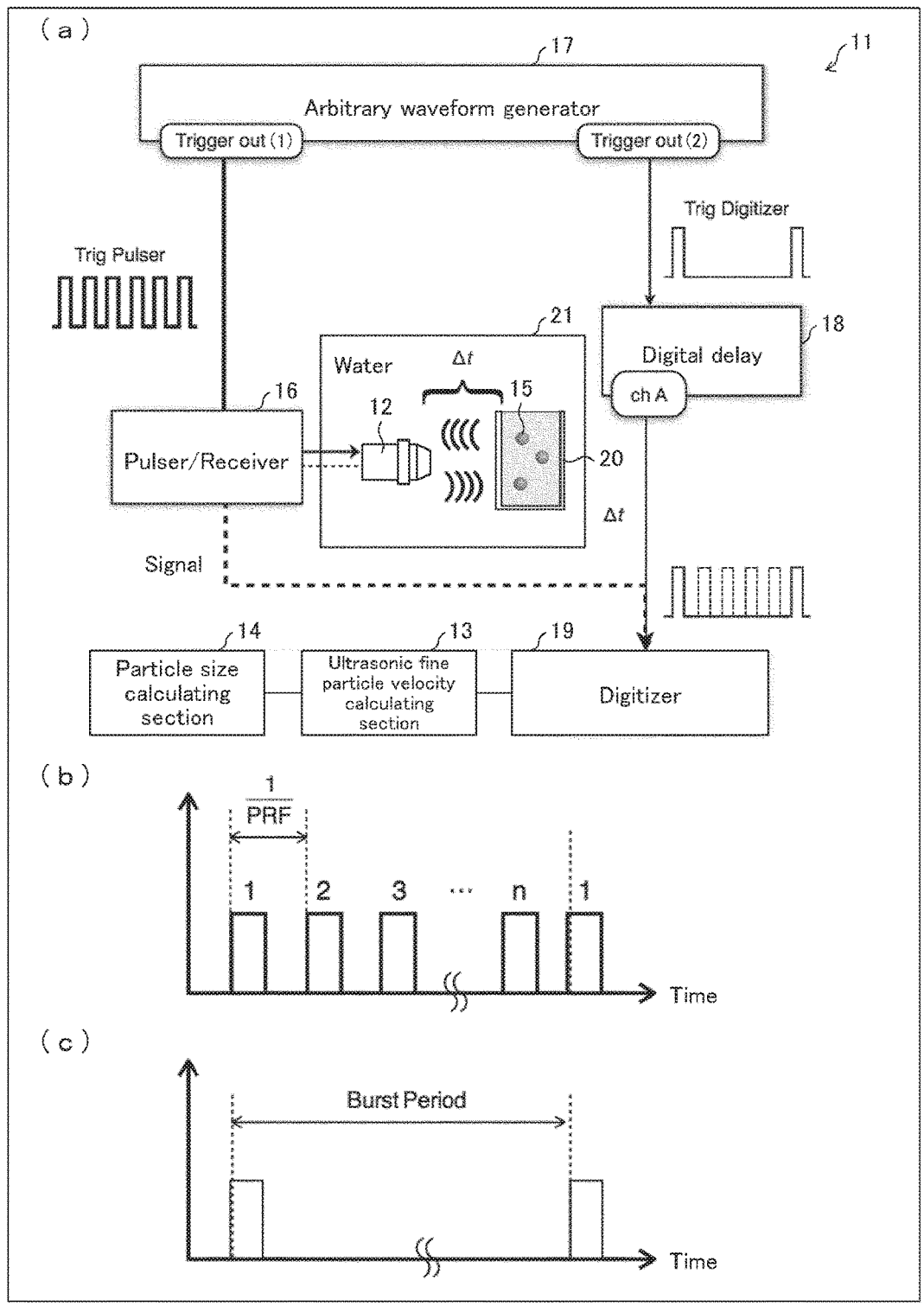

(a) of FIG. 7 is a view schematically illustrating an arrangement of an ultrasonic particle size measurement device in accordance with Embodiment 2. (b) of FIG. 7 is a timing chart of a signal waveform to be supplied to a transducer by a pulser/receiver provided in the ultrasonic particle size measurement device. (c) of FIG. 7 is a timing chart in which a scatter signal that is electrically transduced by a digitizer provided in the ultrasonic particle size measurement device is recorded.

Figure 8:
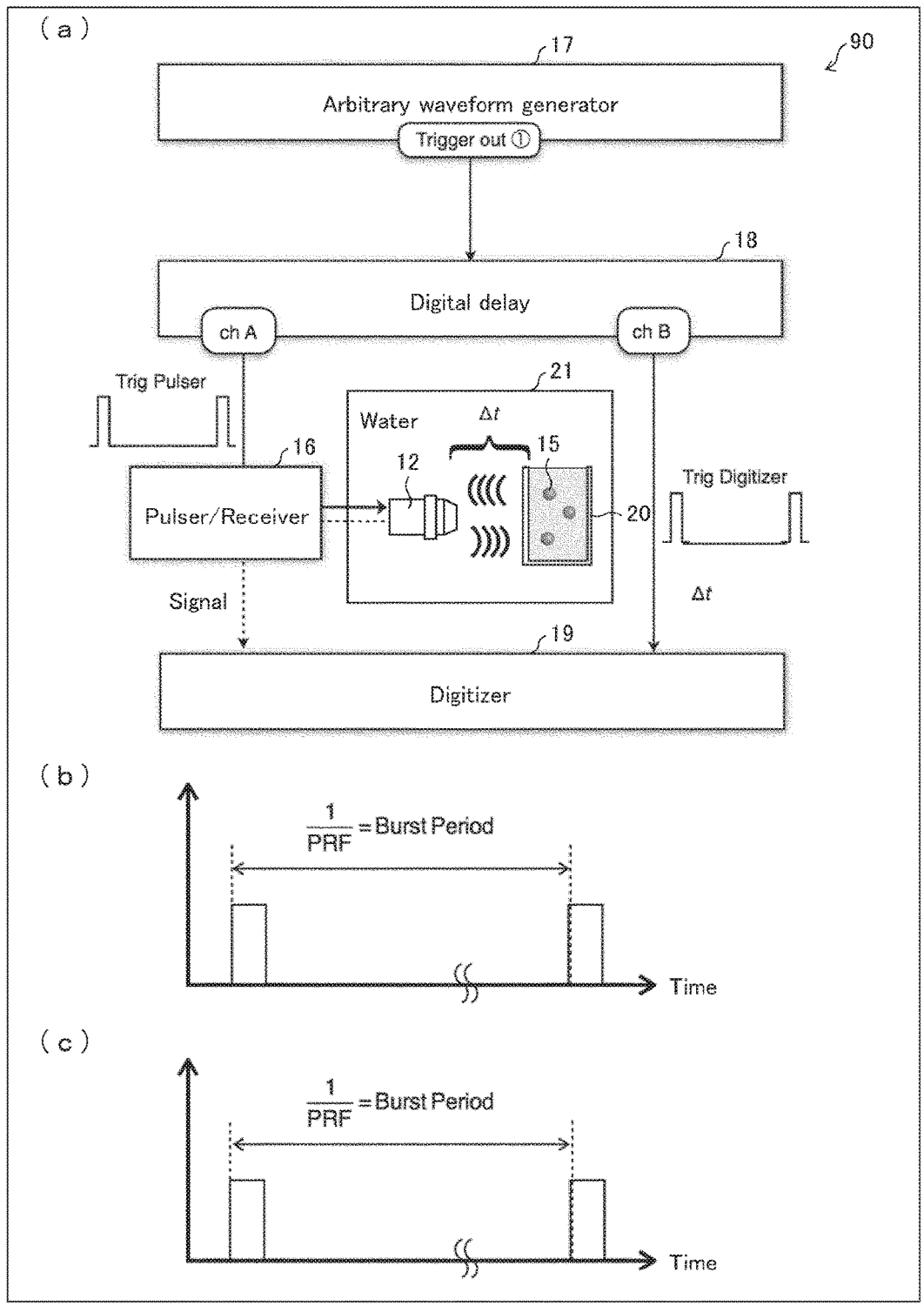

(a) of FIG. 8 is a view schematically illustrating an arrangement of a conventional ultrasonic particle size measurement device. (b) of FIG. 8 is a timing chart of a signal waveform to be supplied to a transducer by a pulser/receiver provided in the ultrasonic particle size measurement device. (c) of FIG. 8 is a timing chart in which a scatter signal that is electrically transduced by a digitizer provided in the ultrasonic particle size measurement device is recorded.

Figure 9:
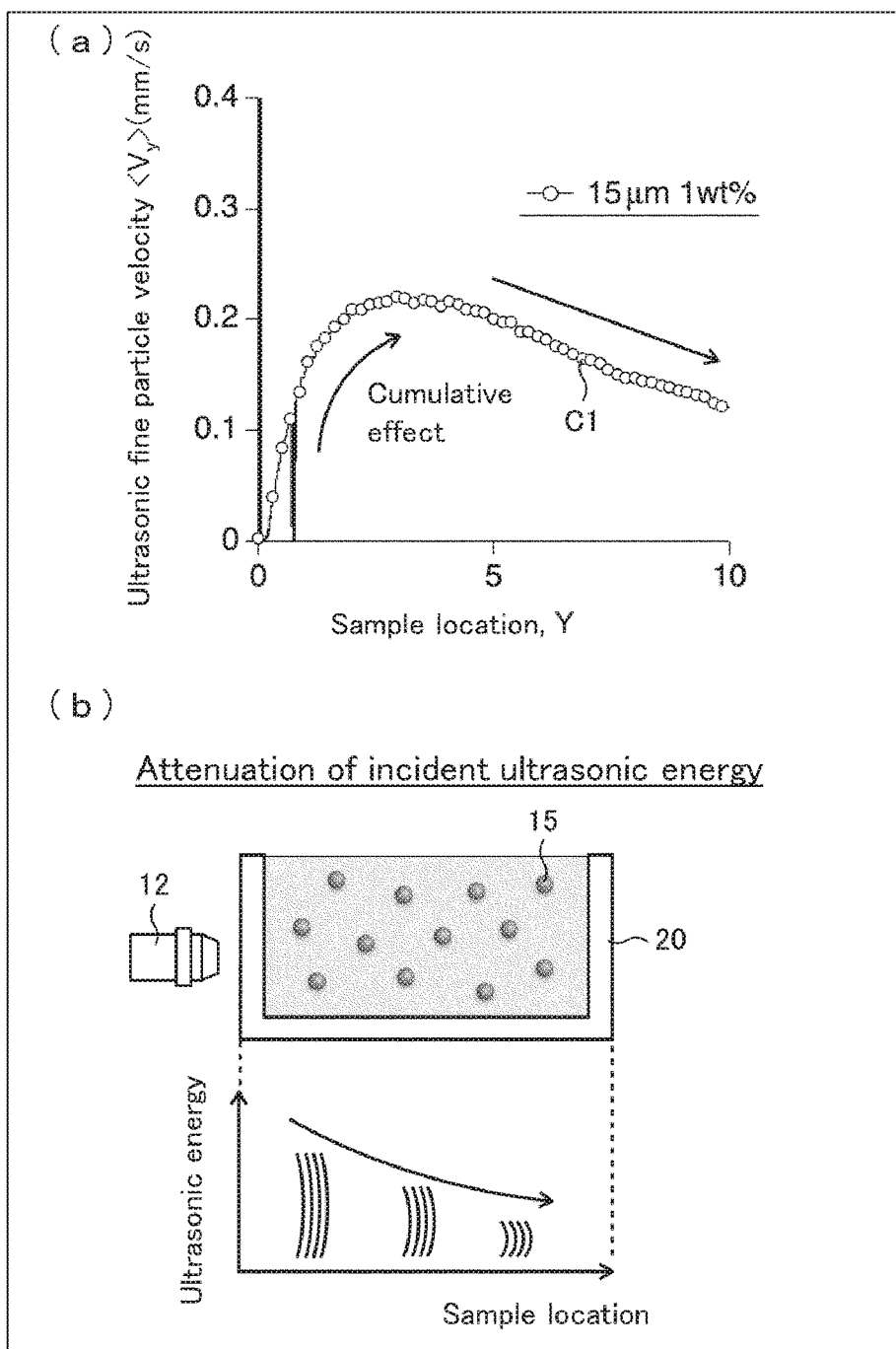

(a) of FIG. 9 shows a graph indicating a relationship between (a) an ultrasonic fine particle velocity calculated by an ultrasonic fine particle velocity calculating section provided in the ultrasonic particle size measurement device in accordance with Embodiment 2 and (b) a sample location. (b) of FIG. 9 is a view for explaining attenuation of ultrasonic energy heading toward a fine particle in a solvent from a transducer provided in the ultrasonic particle size measurement device.

Figure 10:
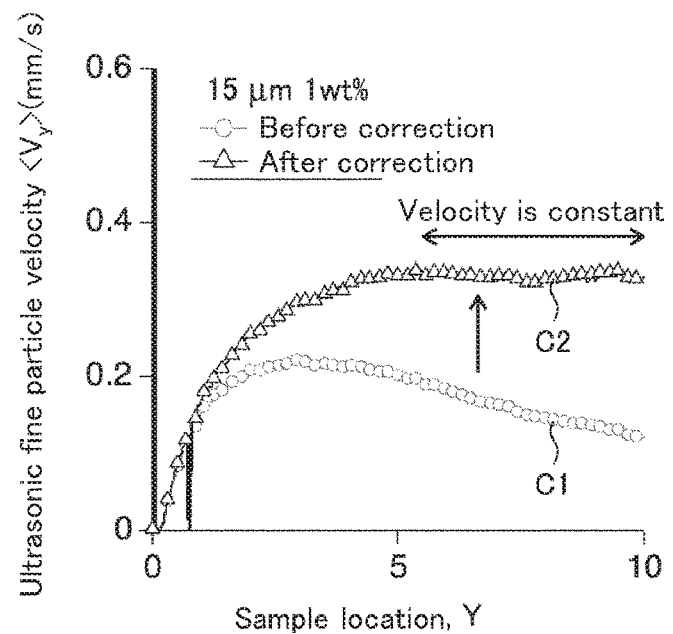

FIG. 10 shows a graph for explaining an aspect in which attenuation of the ultrasonic energy is corrected.

Figure 11:
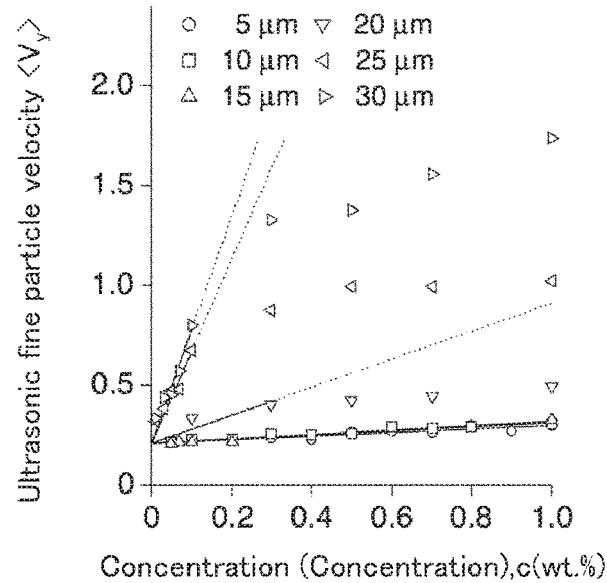

FIG. 11 shows a graph indicating, for each particle size of the fine particle, a relationship between (a) the ultrasonic fine particle velocity and (b) a concentration of the fine particle.

Figure 12:
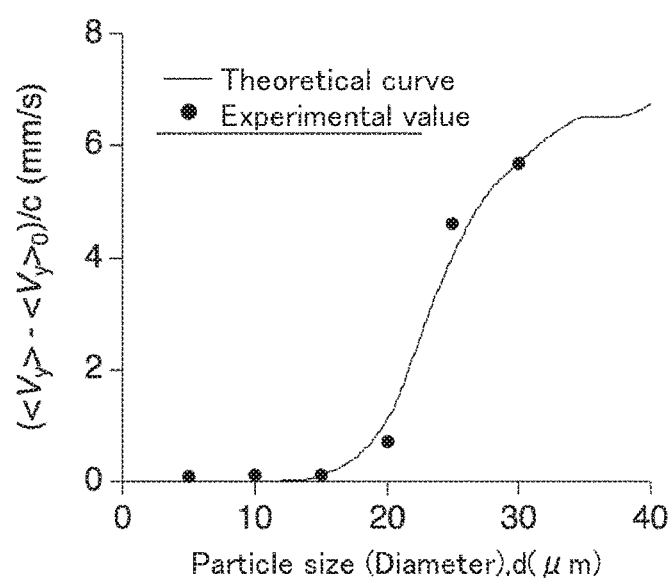

FIG. 12 shows a graph indicating a relationship between (a) a variable for the ultrasonic fine particle velocity and (b) the particle size of the fine particle.

Figure 13:
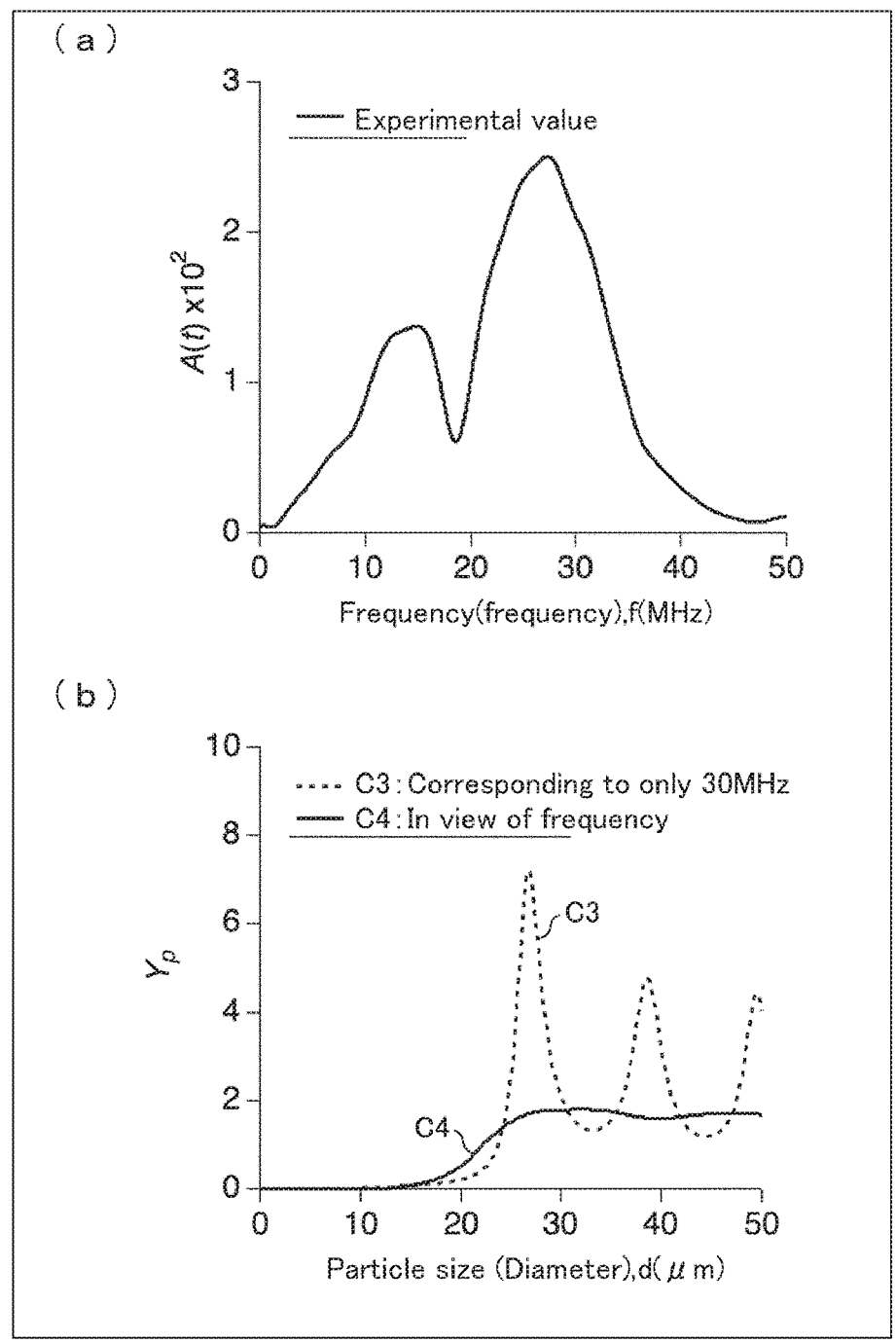

(a) of FIG. 13 shows a graph indicating a frequency characteristic of the transducer. (b) of FIG. 13 shows graphs each indicating particle size dependence of Yp in accordance with Embodiment 2.

Figure 14:
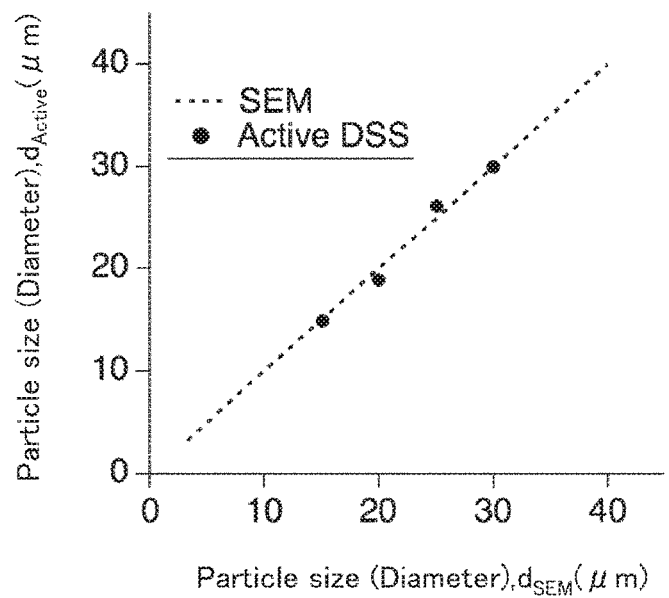

FIG. 14 shows a graph indicating a relationship between (a) a particle size measured by use of the ultrasonic particle size measurement device and (b) a particle size measured by use of a scanning electron microscope.

Figure 15:
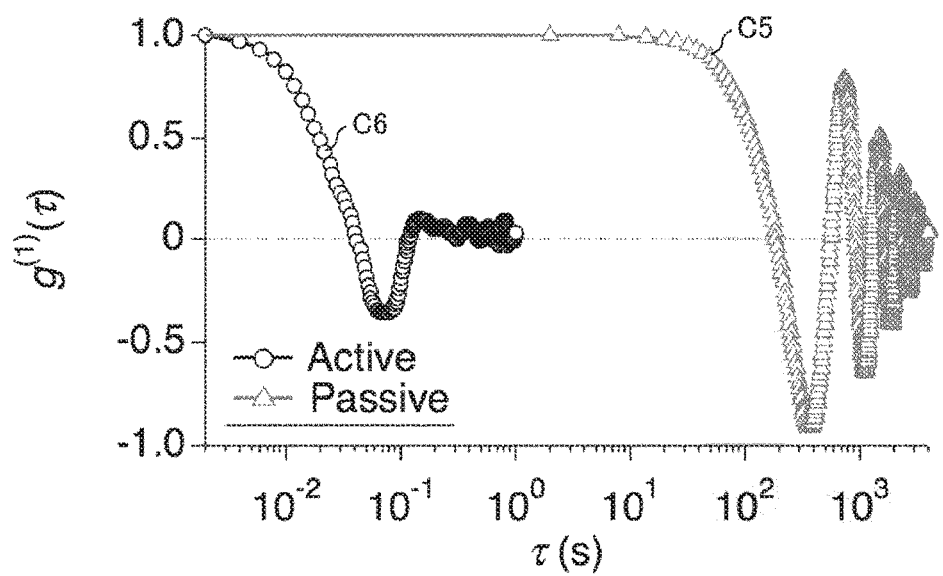

FIG. 15 shows graphs for explaining a difference in measurement time between an ultrasonic particle size measuring method in accordance with Embodiment 2 and a conventional ultrasonic particle size measuring method.

Figure 16:
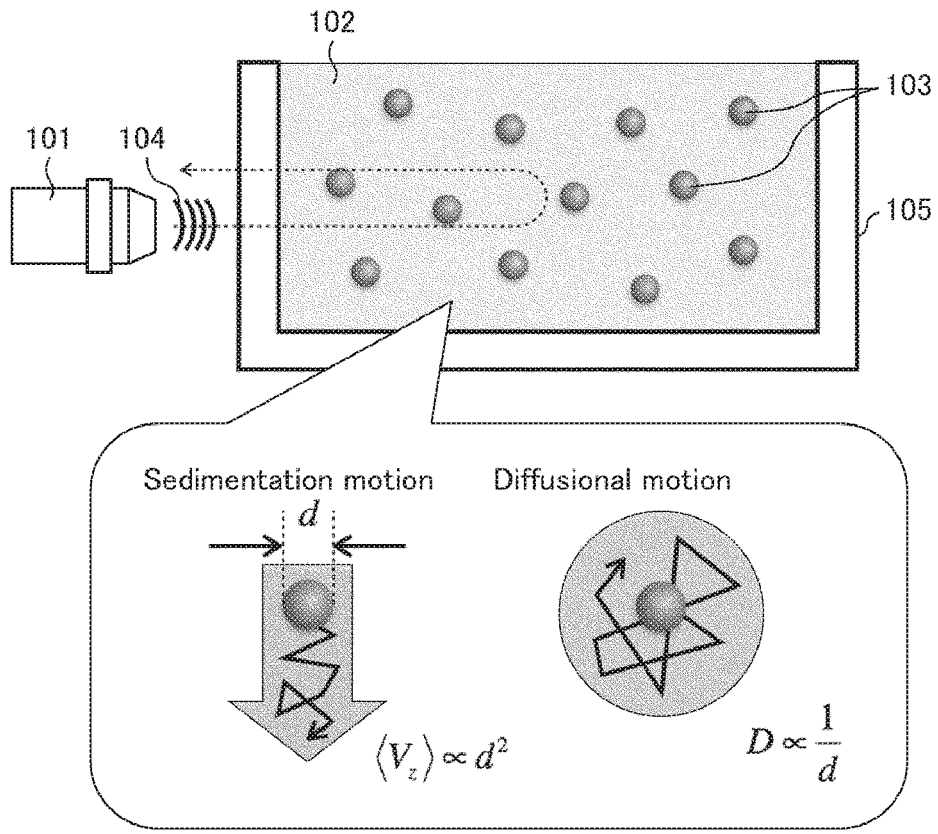

FIG. 16 is a view for explaining a particle size measuring method carried out by a dynamic ultrasound scattering method.

Figure 17:
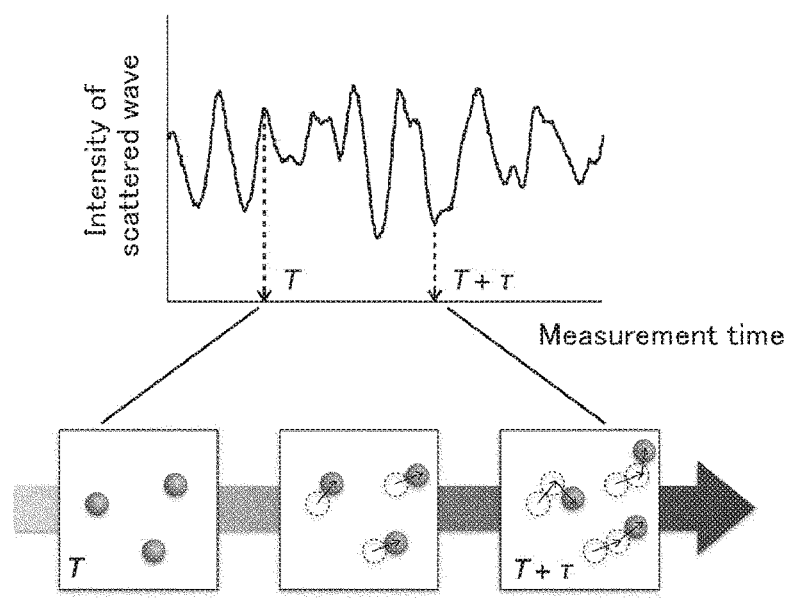

FIG. 17 is a view for explaining a relationship between (a) a change over time in scattered wave and (b) a change in fine particle in the particle size measuring method carried out by the dynamic ultrasound scattering method.

DESCRIPTION OF EMBODIMENTS

The following description specifically discusses an embodiment of the present invention.

Embodiment 1

(Overview of Embodiment 1)

The reason why a measurement error of approximately 10% occurs in a particle size measured by the conventional dynamic ultrasound scattering method (Non-patent Literature 5) is largely due to the fact that emitted light is a laser having a narrow wavelength distribution, whereas an ultrasonic pulse is a "broadband" pulse having a broad wavelength distribution and constituted by an emitted wave containing various frequency components. An ultrasonic pulse that allows various broad frequency bands to be covered by measurement carried out one time is convenient in a spectroscopy experiment in which frequency analysis is carried out. Such a distribution of various frequency components inhibits precise determination of a location of a particle at a given instantaneous time and a particle size. According to Embodiment 1, an ultrasonic pulse obtained along a time axis is subjected to a Fourier transform and analyzed in a frequency space. It has been conventionally known that an operation of a Fourier transform is used. Note, however, that instead of using either an amplitude spectrum or a phase change as usual to process an amplitude or a phase by a center frequency response, it is novel in Embodiment 1 to formulate a perfect correlation function of a complex type and process both an amplitude and a phase by respective correct frequency responses. Actually, a scattering amplitude subjected to a Fourier transform from a time region to a frequency region was analyzed in the past research (Non-patent Literature 6) carried out by the inventors of the present invention. Note, however, that a result of the analysis merely shows a change in velocity compared with a change over time in phase including noise and makes it impossible to accurately find a velocity for finding a particle size. Thus, a found particle size had an error of approximately 10%.

Non-patent Literature 6 and Patent Literature 2 each describe a method for using a lock-in phase method. According to this method, a peak frequency of an ultrasonic pulse having various frequency components is used as a spatial frequency. Note, however, that since a waveform of an ultrasonic pulse is incompletely symmetrical in most cases as described later, a value of a peak frequency gives no correct spatial frequency. Thus, since use of a peak frequency of an ultrasonic pulse as a spatial frequency produces a great error, a new analysis method for overcoming such a problem of production of an error by a peak frequency is necessary for accurate finding of a particle size of a fine particle.

According to Embodiment 1, an average velocity and a particle size can be measured with extremely high accuracy by a method described below.

First, an ultrasonic pulse is emitted to a sample in which a fine particle is present in a liquid. The emitted ultrasonic pulse propagates through the liquid and is scattered by the fine particle. An ultrasonic pulse waveform, which is a first scattering amplitude obtained through the fine particle at a certain observation time (Evolution time) T, is acquired, and the ultrasonic pulse waveform is subjected to a Fourier transform in a direction of a pulse field time (propagation time, Field time) t so that a second scattering amplitude is generated. Then, a real component and an imaginary component of the second scattering amplitude, which consists of a complex number, are found as a function of a frequency f of the ultrasonic pulse. The real component and the imaginary component are converted into an amplitude and a phase, respectively, as needed. In a case where the Fourier transform is carried out for each observation time T, two-dimensional data (matrix data) concerning the observation time T and the frequency f of the ultrasonic pulse is obtained. Next, the second scattering amplitude is transformed into a complex autocorrelation function with respect to a direction of the observation time T. The complex autocorrelation function is calculated by use of a correlative theorem. Specifically, the Fourier transform is further carried out with respect to the second scattering amplitude in the direction of the observation time T so that the second scattering amplitude is transformed into data concerning a characteristic frequency F of the observation time, and thereafter the data obtained after the Fourier transform is multiplied by a complex conjugate form of the data obtained after the Fourier transform, so that the complex autocorrelation function is obtained by an inverse Fourier transform. This causes the data to be replaced with the function of the observation time T. Thus, the data of the complex autocorrelation function serves as a function of the frequency f and a delay time T.

Since each frequency f (and a corresponding scattering vector $q=4\pi f/c$ where c is a known sound velocity) of an ultrasonic pulse is known, a complex autocorrelation function of the each frequency f makes it possible to calculate a motion velocity of a fine particle by use of a correct wavelength. In this regard, a method in accordance with Embodiment 1 is a new method that differs from each of a time domain correlation function method (Non-patent Literature 6, Patent Literature 2, lock-in phase method) with respect to a conventional pulse field time (propagation time) t and an ultrasonic Doppler method, which has been known since a long time ago. The method in accordance with Embodiment 1, which method has a characteristic of having accuracy with which to carry out an experiment on a particle size of a fine particle, achieves a great reduction in measurement error in particle size from approximately 10% of a conventional method to approximately 1% of Embodiment 1.

The method in accordance with Embodiment 1 can also be used, in various ultrasonic wave analyzing methods in each of which a broadband ultrasonic pulse is used, as a method for reversely calculating a main frequency. Specifically, in a case where an ultrasonic pulse is locked in by use of such a correct main frequency (or wavelength), a motion velocity can be measured by use of an ultrasonic phase with high accuracy as already shown in Non-patent Literature 6, and also imaging of a motion velocity can be mapped by use of a highly accurate absolute value.

(Arrangement of Ultrasonic Particle Size Measurement Device 1)

Figure 1:
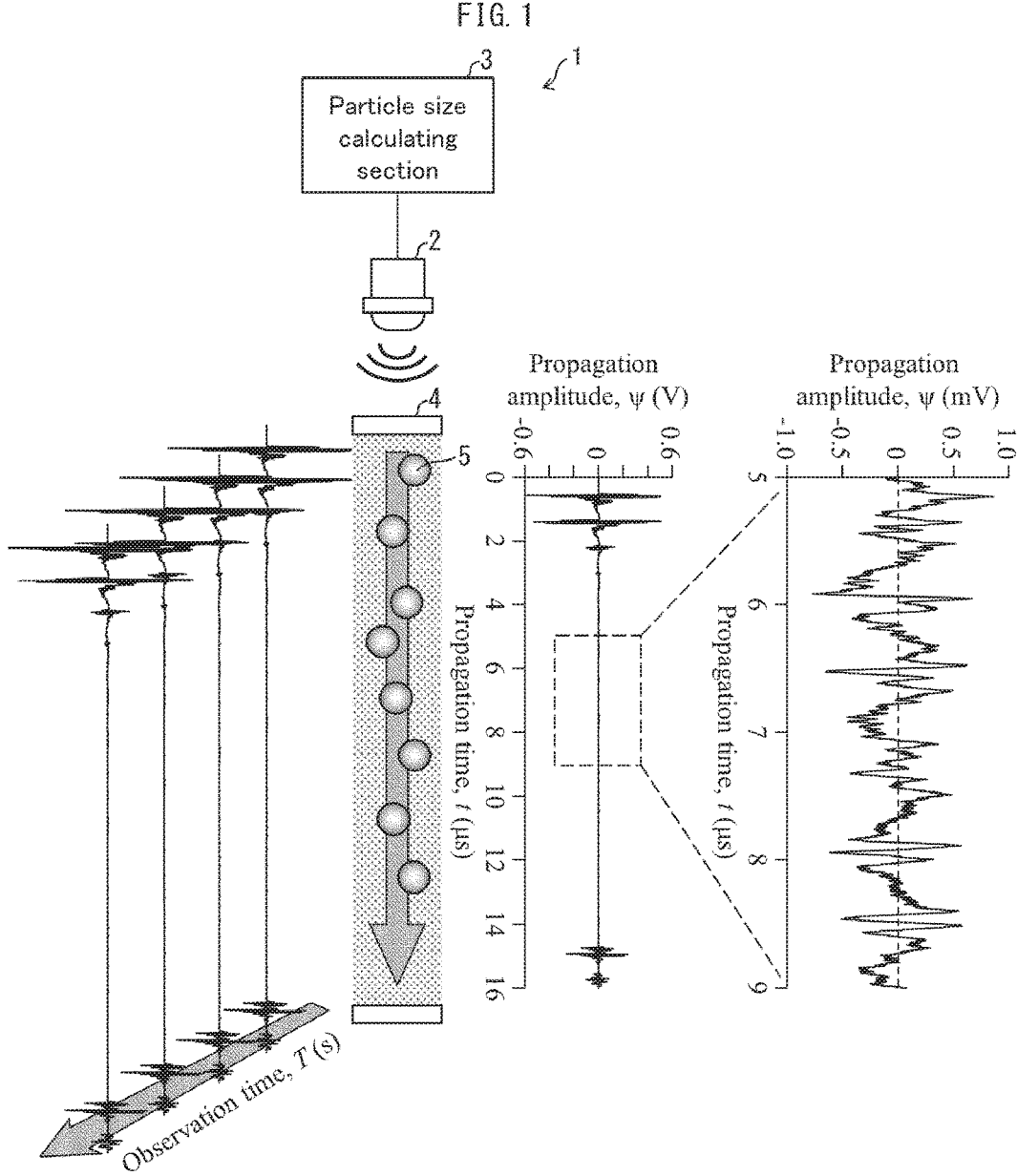
FIG. 1 is a view schematically illustrating an arrangement of an ultrasonic particle size measurement device in accordance with Embodiment 1.

FIG. 1 is a view schematically illustrating an arrangement of an ultrasonic particle size measurement device 1 in accordance with Embodiment 1. The ultrasonic particle size measurement device 1 includes an ultrasonic transducer (also referred to as an "ultrasonic wave transmitter-receiver", hereinafter merely referred to as a "transducer") 2. The transducer 2 is constituted by, for example, a piezoelectric element made of, for example, a piezoelectric ceramic or a piezoelectric crystal, and carries out a function of (i) transforming an electric pulse into an ultrasonic pulse so as to transmit the ultrasonic pulse and (ii) transforming an ultrasonic pulse into an electric pulse so as to receive the electric pulse. First, an ultrasonic pulse is emitted to fine particles 5 sedimenting while being dispersed into a solvent in a cell 4. Then, the transducer 2 receives the ultrasonic pulse which has been scattered by the fine particles 5, transforms the ultrasonic pulse into an electric pulse ($\Psi$ (V) in FIG. 1), generates a first scattering amplitude $\Psi$ (t,T) based on a propagation time t and an observation time T with respect to motion of the fine particles, and supplies the first scattering amplitude $\Psi$ (t,T) to a particle size calculating section 3.

The particle size calculating section 3 generates a second scattering amplitude $\Psi$ (f,T) obtained by subjecting the first scattering amplitude $\Psi$ (t,T) at the observation time T to a Fourier transform in a direction of the propagation time t and calculates an amplitude r (f,T) and a phase $\theta$ (f,T) of the second scattering amplitude $\Psi$ (f,T) in accordance with a real part and an imaginary part, respectively, of the second scattering amplitude $\Psi$ (f,T). Then, the particle size calculating section 3 generates a complex correlation function in accordance with the amplitude r (f,T) and the phase $\theta$ (f,T), calculates a sedimentation velocity of a fine particle in accordance with the complex correlation function, and calculates a particle size of a sedimenting fine particle in accordance with the sedimentation velocity.

(Operation of Ultrasonic Particle Size Measurement Device 1)

The following description discusses an actual flow of analysis and a result of the analysis in accordance with measurement of a particle size of a sedimenting fine particle. FIG. 1 shows typical scattering amplitude waveforms obtained in a dynamic ultrasonic scattering experiment. A waveform on the observer's left shows how a scattering amplitude waveform changes in accordance with the observation time T, whereas a waveform on the observer's right specifically shows one of the scattering amplitude waveforms. Note here that the transducer 2 includes a waveform recording device such as a digitizer. The waveform recording device of the transducer 2 records therein data obtained by transformation, by the transducer 2 into an electric signal, of the ultrasonic pulse emitted to the fine particles 5, scattered, and then returned to the transducer 2.

For example, in a case where a rectangular cell having a depth of 10 mm is used as the cell 4, the cell is filled with a dispersion medium in which particles are dispersed, and a sound velocity of water is used, it is revealed that it takes approximately 13 microseconds for a single ultrasonic pulse to reciprocate in the cell 4. Since a single ultrasonic pulse waveform recorded in the transducer 2 which includes a high-speed digitizer capable of recording at 200 mega samples per second has pulse time resolving power of 5 nanoseconds, the single ultrasonic pulse has approximately 2600 pieces of data. In a case where the transducer 2 which is a transducer for an ultrasonic pulse having a center frequency of 20 MHz causes a digitizer capable of recording at 200 mega samples per second to record one wavelength of an ultrasonic pulse, the one wavelength is made up of 10 pieces of data. A propagation time of the ultrasonic pulse is of an order of microseconds as described earlier. An ultrasonic wave that propagates through water has a wavelength of approximately 75 micrometers in the case of 20 MHz. Thus, in an ultrasonic scattering experiment, it is possible to observe motion of a fine particle in such a minute space scale. Since an observation time required for the observation is of an order of several seconds to several hundred seconds, each ultrasonic pulse looks like a dot when seen in a scale in accordance with a state of motion of a fine particle.

Thus, in the dynamic ultrasonic scattering experiment, the transducer 2 (i) repeatedly applies, to a fine particle at an interval of an order of seconds or milliseconds, an ultrasonic pulse that reciprocates in an order of a dozen or so microseconds and has several thousand pieces of data, and (ii) records therein a state of motion of the fine particle by use of a waveform of an ultrasonic pulse scattered by the fine particle, i.e., the first scattering amplitude. In a case where a propagation time of an ultrasonic pulse is t and an observation time with respect to motion of a fine particle is T, raw data, obtained by the transducer 2, concerning an ultrasonic pulse scattered after being emitted to a sedimenting fine particle is a function of the propagation time t and the observation time T and is described as the first scattering amplitude $\Psi$ (t,T).

According to Non-patent Literature 5, which is a conventional technique, an autocorrelation function defined by the following Equation (3) is found.

[Math. 3]

$$g^{(1)}(\tau, t) = \frac{\langle \psi(t, T)\psi^*(t, T+\tau)\rangle_T}{\langle \psi(t, T)\psi^*(t, T)\rangle_T} \qquad \text{Equation (3)}$$

Note here that in Equation (3), $\tau$ means a delay time (correlation time), t means a pulse arrival time (corresponding to a location by being multiplied by a sound velocity), T means the observation time, * means a complex conjugate, $\langle \ldots \rangle_T$ means an average over the observation time, and $\Psi$ (t,T) means the first scattering amplitude.

Note here that $\Psi$ (t,T) is a voltage value of a scattered waveform observed in a digitizer (or an oscilloscope), the voltage value being read by the digitizer, and is stored in a form of real data. Thus, though a function form of an autocorrelation function $g^{(1)}$ ($\tau$,t) found by Equation (3) is also a complex number, the autocorrelation function $g^{(1)}$ ($\tau$,t) found by Equation (3) results in a real number because $\Psi$ (t,T) is real data.

(a) of FIG. 2 shows a graph schematically indicating the first scattering amplitude $\Psi$ (t,T) measured by use of the ultrasonic particle size measurement device 1 of Embodiment 1. (b) of FIG. 2 shows a graph schematically indicating the second scattering amplitude (f,T) measured by use of the ultrasonic particle size measurement device 1 of Embodiment 1. The following description explains that a correlation function used in Embodiment 1 totally differs from a conventional correlation function.

First, the particle size calculating section 3 of the ultrasonic particle size measurement device 1 in accordance with Embodiment 1 (i) subjects the first scattering amplitude $\Psi$ (t,T), obtained by the transducer 2 and shown in (a) of FIG. 2, to a Fourier transform in a direction of the propagation time t of an ultrasonic pulse, and (ii) generates the second scattering amplitude $\Psi$ (f,T) of (b) of FIG. 2. Then, assume that a real part and an imaginary part of the second scattering amplitude $\Psi$ (f,T), which is a complex number, are a and b, respectively. In this case, the following Equation (4) is obtained.

[Math. 4]

$$\Psi(f,T) = a(f,T) + ib(f,T) \qquad \text{Equation (4)}$$

Note here that in Equation (4), $\Psi$ (f,T) is the second scattering amplitude, a and b are the real part and the imaginary part, respectively, of the second scattering amplitude, and f is a frequency of an ultrasonic pulse.

The particle size calculating section 3 finds, in accordance with Equation (4), an amplitude r ($\omega$,T) and a phase $\theta$ ($\omega$,T) as shown in the following Equation (5) and Equation (6), respectively.

[Math. 5]

$$r(f,T) = \sqrt{a^2 + b^2} \qquad \text{Equation (5)}$$

Note here that in Equation (5), r represents a magnitude (amplitude) of the second scattering amplitude $\Psi$.

[Math. 6]

$$\theta(f, T) = \tan^{-1}\left(\frac{b}{a}\right) \qquad \text{Equation (6)}$$

Note here that in Equation (6), $\theta$ is a phase of a second scattering function $\Psi$, and $\tan^{-1}$ is an inverse function of tan.

Then, in a case where the particle size calculating section 3 solves the following Equation (7), matrix data (complex two-dimensional data) with respect to the frequency f of the ultrasonic pulse and the observation time T is obtained as illustrated in (b) of FIG. 2.

[Math. 7]

$$\psi(f, T) = r(f, T)\exp\left[i\tan^{-1}\frac{\sin\theta(f, T) - \langle\sin\theta\rangle_T(f)}{\cos\theta(f, T) - \langle\cos\theta\rangle_T(f)}\right] \qquad \text{Equation (7)}$$

The matrix data is complex two-dimensional data showing that dependence of the scattering amplitude on the frequency f is changed in correspondence with the observation time T of the fine particle. Then, the particle size calculating section 3 fixes each frequency f and uses the correlative theorem in the direction of the observation time T so as to find a complex correlation function $g^{(1)}$ (f,T) defined by the following Equation (8).

[Math. 8]

$$g^{(0)}(f, \tau) = \frac{\langle \psi(f, T)\psi^*(f, T+\tau)\rangle_T}{\langle \psi(f, T)\psi^*(f, T)\rangle_T} \qquad \text{Equation (8)}$$

Specifically, as described below, the particle size calculating section 3 subjects the second scattering amplitude $\Psi$ (f,T) to a Fourier transform from the observation time T into the frequency f this time so as to cause the second scattering amplitude Ψ to be Ψ (f,F). Then, the particle size calculating section 3 multiplies Ψ (f,F) by a conjugate Ψ* (f,F) and then subjects Ψ (f,F), multiplied by the conjugate Ψ* (f,F), to an inverse Fourier transform so as to obtain a complex correlation function. Subsequently, the particle size calculating section 3 calculates a sedimentation velocity of a fine particle 5 in accordance with the complex correlation function and calculates a particle size of the fine particle 5 in accordance with the sedimentation velocity. Note here that in the following expression, FFT means a fast Fourier transform, and IFFT means an inverse fast Fourier transform.

[Math. 9]

$$\begin{cases} \psi(f,T) \xrightarrow[FFT]{} \psi(f,F) \\ \psi(f,T)\psi^*(f,T+\tau) \xleftarrow[FFT]{} \psi(f,F) \times \psi^*(f,F) \end{cases}$$

That is, in contrast to a conventional technique in which a particle size is found by finding a real correlation function shown in (a) of FIG. 2, according to Embodiment 1, a particle size is found by finding a complex correlation function shown in (b) of FIG. 2.

According to Non-patent Literature 7, in order that a particle size of a fine particle in Brownian motion is measured, a first scattering amplitude Ψ (t,T) obtained by a transducer is transformed into a second scattering amplitude (f,T) as in the case of Embodiment 1. Note, however, that Non-patent Literature 7 significantly differs from Embodiment 1, in which Equation (7), which is a complex correlation function based on both an amplitude and a phase, is solved, in that in Non-patent Literature 7, a real correlation function of only an amplitude is found based on the following reference equation obtained by excluding a phase part in Equation (7) of Embodiment 1.

Ψ(f,T)=r(f,T)  (reference equation)

Since a fine particle in Brownian motion which fine particle is to be measured in Non-patent Literature 7 is in random motion around a reference position, the fine particle has no motion component in a specific direction. This makes it possible to regard an average of quantities of motion of the fine particle as zero. Thus, in such a case, according to the method of Non-patent Literature 7, a phase term indicative of a quantity of motion of the fine particle is ignored, and data is processed by use of merely a real correlation function (the above reference equation) in which the phase part is excluded.

Note, however, that in contrast to a fine particle whose main motion is Brownian motion, a sedimenting fine particle has an average motion component that falls in a direction of gravity while fluctuating. It is a matter of course that strictly speaking, a fine particle whose main motion is Brownian motion for a short time also has an average motion component. Thus, the inventors of the present invention considered that such systematic analysis of a phase as described earlier is necessary for such evaluation of the average motion component which evaluation is critical to strict measurement and measurement of a particle size of a sedimenting fine particle. As a result of study, the inventors focused on the point that a phase part of a complex correlation function is important to the average motion component. According to Embodiment 1, the particle size calculating section 3 calculates a sedimentation velocity and a particle size of a fine particle in accordance with Equation (7), which is a complex correlation function based on both an amplitude and a phase. As described above, the method of Embodiment 1 and the method in accordance with Non-patent Literature 7 which method is targeted at Brownian motion continuing for a relatively long time totally differ in mathematical expression and processing method.

(a) of FIG. 3 shows a graph indicating a correlation function obtained by a time domain correlation function method which is a conventional technique. (b) of FIG. 3 shows a graph indicating a correlation function obtained by a method which is a conventional technique and in which calculation is carried out in view of a real part of a scattering amplitude influenced by an ultrasonic pulse. (c) of FIG. 3 shows a graph indicating a complex correlation function measured by use of the ultrasonic particle size measurement device 1 of Embodiment 1 of the present invention.

FIG. 3 summarizes some decisive points of difference from the conventional method. (a) of FIG. 3 shows a conventional correlation function obtained without consideration for a frequency distribution included in a pulse. This function is a function obtained by multiplying attenuation of an exponential function and oscillation of a cosine (see the following Equation (9)).

[Math. 10]

$$g^{(1)}(t,\tau)=\cos(q\langle V_z\rangle_T(t)\tau)\exp(-\tfrac{1}{2}q^2\langle \delta V_z^2\rangle_T(t)\tau^2) \quad \text{Equation (9)}$$

Note here that in Equation (9), q represents a scattering vector, $\langle V_z \rangle$ represents an apparent average sedimentation velocity of a fine particle, and $\langle \delta V_z^2 \rangle$ represents statistical dispersion of the apparent average sedimentation velocity.

Application of a known coefficient to this equation makes it possible to obtain, from a cosine term, the average sedimentation velocity <Vz> of the fine particle which average sedimentation velocity is defined by various pulse field times (propagation times). Note, however, that experimental accuracy of the average sedimentation velocity <Vz> of the fine particle, which average sedimentation velocity is obtained by use of Equation (9), is approximately 10%. A particle size is found by substituting the obtained average sedimentation velocity <Vz> into Equation (9). Note, however, that q in Equation (9) is a scattering vector given by the following Equation (10).

[Math. 11]

$$q = \frac{4\pi}{\lambda}\sin\frac{\theta}{2} = \frac{4\pi f}{V_p}\sin\frac{\theta}{2} \quad \text{Equation (10)}$$

Note here that in Equation (10), λ represents a wavelength of an ultrasonic pulse, θ represents a scattering angle, and $V_p$ represents a phase sound velocity (herein may also be simply a "sound velocity").

As a representative value of the frequency f, a value of a center frequency of a broadband pulse is used. Note that an ultrasonic wave, which has a greater wavelength than light or an X-ray, has a great coherence length (difference in optical path length which difference is obtained by measuring to what optical path lengths interference fringes appear). Thus, an ultrasonic wave has been used for measurement of a particle size of a fine particle because a less great error is caused even by use of a broadband pulse. In a case where an error of 10% (described earlier) is allowable, such a conventional method in which an ultrasonic wave is used is usable but has a problem in achievement of measurement of a particle size with higher accuracy.

Next, the following description discusses, with reference to (b) of FIG. 3, a result of use of a Fourier transform (of a megahertz ultrasonic wave) from t to f in Non-patent Literature 7 (Igarashi 2014). According to Non-patent Literature 7, a Fourier transform into a frequency space is carried out, but a correlation function of a scattering amplitude is merely simply found based on a result of the Fourier transform into the frequency space, and a phase is not considered. (b) of FIG. 3 shows a graph of a correlation function found with respect to a silica particle having a particle size d of 500 nm, and a diffusion coefficient is calculated by use of an exponential function expressed by the following Equation (11).

[Math. 12]

$$g^{(1)}(\tau) = \exp(-Dq^2\tau) \qquad \text{Equation (11)}$$

Equation (11) is a so-called exponential function whose parameter is a linear equation of time. Meanwhile, the conventional method carried out with respect to a sedimenting particle is a Gaussian function, such as Equation (9), whose parameter is a quadratic equation of time. The exp and a cosine function that gives an average velocity constitute a correlation function. As described above, theoretical formulae (Equation (10) and Equation (11)) processed in Non-patent Literature 7 totally differ from a theoretical formula (Equation (6)) processed in Embodiment 1. In the case of Brownian motion, a particle size is found by applying an obtained diffusion coefficient to the aforementioned Stokes-Einstein's equation expressed by Equation (1).

(c) of FIG. 3 shows an example of a complex correlation function obtained in Embodiment 1. It is revealed that the complex correlation function, which is obtained by transformation, into a frequency space, the matrix data obtained by solving Equation (7), makes it possible to reproduce components of both a cosine function that gives an average sedimentation velocity given by the following Equation (12) and a Gaussian function that gives a fluctuation in velocity.

[Math. 13]

$$g^{(1)}(f, \tau) = \cos(q\langle V_z\rangle_T(f)\tau)\exp\left(-\frac{1}{2}q^2\langle \delta V_z^2\rangle_T(f)\tau^2\right) \qquad \text{Equation (12)}$$

$$\left\{q = \frac{4\pi f}{c}\sin\left(\frac{\theta}{2}\right)\right\}$$

The following description discusses, with reference to a complex correlation function represented by Equation (12), how to obtain a particle size of a fine particle.

First, the average sedimentation velocity $\langle V_z\rangle$ of the fine particle is obtained by applying Equation (12) to a non-linear least-squares method. Note here that a scattering vector q is found based on Equation (9). Note that an analysis method in accordance with Embodiment 1 has a characteristic such that the frequency f in Equation (12) is correctly understood in advance. A conventional analysis method differs from the analysis method in accordance with Embodiment 1 in that the frequency f at its peak is used in the conventional analysis method.

After the average sedimentation velocity $\langle V_z\rangle$ is obtained, a graph of FIG. 5 which graph indicates particle concentration dependence of a sedimentation velocity is drawn. Next, a volume fraction φ is extrapolated by use of zero so that a sedimentation velocity $V_0$ of one fine particle is obtained. For example, in a case where an experiment can be carried out in a region at a low concentration, the sedimentation velocity $V_0$ is found by linear extrapolation and based on $\langle Vz\rangle = V_0(1-A\varphi)$. Note here that A is an inclination of a straight line. Note that the sedimentation velocity $V_0$ can also be found by use of an exponent n of an RZ (Richardson-Zaki) function and based on a well-known empirical formula such as $\langle Vz\rangle = V_0(1-\varphi)^n$.

In a case where the sedimentation velocity $V_0$ is thus found, it is possible to calculate a diameter d of a fine particle in accordance with Equation (2).

It is revealed that the graph of (c) of FIG. 3 is more accurately found than the graph of (a) of FIG. 3. The complex correlation function of (c) of FIG. 3 decisively differs from the conventional correlation function of (a) of FIG. 3 in that the complex correlation function of (c) of FIG. 3 makes it possible to obtain data for each frequency of a broadband pulse (i.e., allows calculation of data for each frequency of a broadband pulse not by merely using an incorrect average scattering vector q calculated by using a value of a center frequency of a broadband pulse not as a representative value of the frequency f, but by determining a scattering vector q correctly corresponding to each frequency f. That is, Embodiment 1 has a characteristic of being independent of an assumption that a value of a center frequency is employed as in the conventional correlation function of (a) of FIG. 3. It will be discussed later in a place where FIG. 4 is described that such a conventional assumption that a value of a center frequency is employed is a cause of an error.

(a) and (b) of FIG. 4 show graphs comparing (a) a result of measurement, by the ultrasonic particle size measurement device 1, of a sedimentation velocity of polymer particles dispersed into water and (b) a result of measurement, by an ultrasonic particle size measurement device having a conventional arrangement, of a sedimentation velocity of polymer particles dispersed into water. FIG. 4 summarizes a result of measurement of a sedimentation velocity at which together with a surfactant SDS, polymer particles (polydivinylbenzene particles) having a particle size of 10 micrometers were actually dispersed into water. As is clear from (b) of FIG. 4, it is revealed that a sedimentation velocity analyzed by a frequency domain correlation function method in accordance with Embodiment 1 is independent of a frequency.

(a) of FIG. 4 shows frequency components of ultrasonic pulses obtained in a case where two types of totally different transducers, which are a transducer B20K2I (50 pF) and a transducer 25C6I (500 pF). In (a) of FIG. 4, a vertical axis shows an amplitude of an ultrasonic pulse, and a horizontal axis shows a frequency contained in the ultrasonic pulse. In a case where a glance is casted on (a) of FIG. 4, a frequency component whose amplitude reaches its peak (frequency component corresponding to "○" in (a) of FIG. 4) apparently seems to be a main frequency component.

(b) of FIG. 4 shows a difference in result of analysis of an average sedimentation velocity in a case where the above two sensors are used and different analysis methods (the time domain correlation function method and the lock-in phase method), which are two old methods, are used. In (b) of FIG. 4, the vertical axis shows the average sedimentation velocity $\langle Vz\rangle$, which is critical to evaluation of a particle size, and the horizontal axis shows a frequency used to calculate the average sedimentation velocity $\langle Vz\rangle$.

A result, appended to (b) of FIG. 4, of measurement of a sedimentation velocity by a conventional correlation function method is interesting. Transformation of an obtained correlation function into an average sedimentation velocity and a particle size requires a frequency of an ultrasonic pulse. Note, however, that a peak frequency value (described earlier) has been conventionally used for the transformation. Note here that (b) of FIG. 4 shows a result of calculation of an average sedimentation velocity by use of various frequency values including a peak. As is clear from (b) of FIG. 4, the average sedimentation velocity is greatly underestimated in a case where a frequency value higher than the peak and its vicinity is used, whereas the average sedimentation velocity is greatly overestimated in a case where a frequency value lower than the peak and its vicinity is used. Note, however, that it is revealed that an error of approximately 10% occurs in a case where a frequency value f near a peak of a spectrum intensity shown in the graph of (b) of FIG. 4 (a frequency value corresponding to "○" in (b) of FIG. 4) is used. That is, it is revealed that an error is made greater in a case where an average sedimentation velocity and a particle size of a fine particle are calculated by use of a peak frequency (center frequency).

There is a conventional lock-in phase method which is different from the correlation function method shown in (a) of FIG. 3 and in which a phase is extracted from a pulse field (propagation time) illustrated in FIG. 1. According to the lock-in phase method, it is also revealed that though a frequency is locked in near a center frequency, a different sedimentation velocity value is eventually shown because various frequency components are mixed in data obtained before the lock-in. Thus, it follows that the conventional lock-in phase method cannot be used as long as a frequency to lock in is unknown. Note here that the lock-in phase method is an analysis method in which a signal desired to be analyzed is multiplied by a sine wave of a certain frequency so that a signal component corresponding to a frequency component of the signal is extracted, and a technique for extracting especially a phase by use of the analysis method is referred to as a lock-in phase method (see Non-patent Literature 6).

That is, (b) of FIG. 4 also means that use of a frequency that can be found in Embodiment 1 allows a more accurate particle velocity and a more accurate particle size to be obtained even by a conventional method.

(Variation of Embodiment 1)

A variation of Embodiment 1 proposes, as another merit of the present invention, a method for combining the frequency domain correlation function method in accordance with Embodiment 1 with the lock-in phase method. According to the lock-in phase method, an average frequency is merely unknown even near a peak, and data in which information in each moment has been extracted can be obtained.

A frequency corresponding to an intersection of (i) a curve indicative of a sedimentation velocity (showing a correct value irrespective of a frequency) of a fine particle which sedimentation velocity is obtained by the correlation function method in accordance with Embodiment 1 and (ii) a curve indicative of data studied by changing a lock-in frequency serves as a true frequency value. Thus, in a case where a frequency corresponding to an intersection of (i) a curve of the time domain correlation function method (Non-patent Literature 5) (see (b) of FIG. 4) or a curve of the lock-in phase method (Non-patent Literature 6) (see (b) of FIG. 4) and (ii) the curve of the frequency domain correlation function method in accordance with Embodiment 1 is subjected to feedback to the time domain correlation function method or the lock-in phase method again, it is possible to calibrate the time domain correlation function method or the lock-in phase method, so that the feedback can be utilized in various analyses (Non-patent Literature 5, Non-patent Literature 6).

FIG. 5 shows a graph indicating particle concentration dependence of a sedimentation velocity analyzed by use of the lock-in phase method calibrated by the method in accordance with Embodiment 1.

FIG. 5 shows a result of analysis of particle concentration dependence of a sedimentation velocity by use of the lock-in phase method calibrated by the method in accordance with Embodiment 1. It is considered that a value that is linearly extrapolated to zero in a low concentration region is a velocity at which one fine particle sediments, i.e., a stokes velocity $V_0$.

FIG. 6 shows a graph indicating a relationship between (a) a particle size measured by use of the ultrasonic particle size measurement device 1 and (b) a particle size measured by use of a scanning electron microscope (SEM).

As shown in FIG. 6 and Table 1, respective values of accuracy and precision each of which values are obtained by converting the stokes velocity $V_0$ into the particle size d in accordance with Equation (2) are each within 1%, which matches information obtained by FE-SEM. Data of a particle size $d_{SEM}$ obtained by FE-SEM is data obtained by (i) enlarging several hundred fine particles to fill an entire screen so as to obtain a sufficient resolution and recording those fine particles, and (ii) separately calculating respective particle sizes of the fine particles and then finding an average particle size. In a case where the frequency domain correlation function method in accordance with Embodiment 1 is used, a particle size $d_{DSS}$ can be calculated while (i) fine particles are being dispersed in water without the need to carry out dilution and to dry the fine particles and (ii) an error, related to experimental accuracy and precision, of 1% is caused to the particle size $d_{SEM}$ obtained by FE-SEM.

TABLE 1

|  | FE-SEM (μm) | DSS (μm) | Accuracy |
|---|---|---|---|
| Silica 3 μm | 2.91 | 2.91 | 0% |
| Silica 10 μm | 9.57 | 9.54 | 0.3% |
| PDVB 10 μm | 9.48 | 9.41 | 0.6% |

Embodiment 2

(Overview of Embodiment 2)

Embodiment 2 allows particle size measurement to be carried out at a higher S/N ratio and in a shorter time in a case where a particle moves at an extremely low velocity. Embodiment 2 proposes a method in which great ultrasonic energy is intentionally externally applied to fine particles (dispersoids) dispersed into a liquid (dispersion medium) and a particle size of the fine particles is calculated from a velocity (ultrasonic fine particle velocity) induced in the fine particles by the application of the ultrasonic energy. Note that the conventional dynamic ultrasound scattering method in which a particle size is found in accordance with a sedimentation velocity is a simple and easy particle size measuring method with respect to a fine particle. Note, however, that according to the conventional dynamic ultrasound scattering method, it is necessary to start measurement after waiting for a fine particle to reach a state of steady motion. Thus, a fine particle having a smaller particle size and a liquid having a higher viscosity require a longer time for measurement, and in measurement of a fine particle having approximately 3 µm, it is necessary to wait for approximately not less than 20 minutes. In contrast, according to Embodiment 2, the applied ultrasonic energy induces a powerful flow field, and a force exerted on a fine particle in accordance with the ultrasonic energy immediately achieves a balance with a frictional force. Thus, unlike the conventional dynamic ultrasound scattering method, Embodiment 2 makes it unnecessary to wait for measurement for a long time until a fine particle reaches a state of steady motion. The following description may refer to the conventional dynamic ultrasound scattering method as a "passive mode dynamic ultrasound scattering method" and may refer to the dynamic ultrasound scattering method in accordance with Embodiment 2 as an "active mode dynamic ultrasound scattering method".

(Arrangement of Ultrasonic Particle Size Measurement Device 11 in Accordance with Embodiment 2)

(a) of FIG. 7 is a view schematically illustrating an arrangement of an ultrasonic particle size measurement device 11 in accordance with an embodiment. (b) of FIG. 7 is a timing chart showing a timing at which a pulser/receiver 16 provided in the ultrasonic particle size measurement device 1 supplies a driving signal to a transducer 12. (c) of FIG. 7 is a timing chart in which a scatter signal that is an output of the pulser/receiver 16 and is electrically transduced is recorded by a digitizer 19 provided in the ultrasonic particle size measurement device 1. The following description gives respective identical reference signs to members carrying out respective identical functions.

In (a) of FIG. 7, fine particles 15 dispersed into a solvent (dispersion medium) are contained in a cell 20. The cell 20 is provided in water contained in the water tank 21. The ultrasonic particle size measurement device 11 includes the transducer (an ultrasonic energy applicator, an ultrasonic scattered wave receiver) 12. The transducer 12 is provided in the water contained in the water tank 21, and applies, in a direction intersecting a direction (vertical direction in (a) of FIG. 7) in which the fine particles 15 in the function cell 20 sediment, ultrasonic energy so as to serve as an ultrasonic energy applicator for inducing, in the fine particles 15, a fine particle velocity influenced by an ultrasonic wave. The transducer 12 also serves as an ultrasonic scattered wave receiver for receiving an ultrasonic scattered wave scattered by the fine particles 15 in which an ultrasonic fine particle velocity has been induced. Specifically, the transducer 12, which serves as both the ultrasonic energy applicator and the ultrasonic scattered wave receiver in (a) of FIG. 7, can be separated into two transducers that serve as a transmitter and a receiver, respectively.

The ultrasonic particle size measurement device 11 includes an arbitrary waveform generator 17, the pulser/receiver 16, a digital delay 18, and the digitizer 19. The arbitrary waveform generator 17 generates a timing pulse, shown in (b) of FIG. 7, for an ultrasonic wave output by the pulser/receiver 16, and supplies the timing pulse to the pulser/receiver 16. The arbitrary waveform generator 17 also generates a timing pulse, shown in (c) of FIG. 7, for the digitizer 19, and supplies the timing pulse to the digital delay 18. The digital delay 18 delays the timing pulse for the digitizer 19 so as to record a scattered waveform electrically transduced by the digitizer 19. Note that 1/PRF shown in (b) of FIG. 7 is an interval between bursts (Burst Period), the bursts corresponding to a timing pulse for an ultrasonic wave output by which timing pulse the transducer 12 outputs an ultrasonic wave.

The arbitrary waveform generator 17 causes a first trigger out (Trigger out (1)) to supply, to the pulser/receiver 16, a timing pulse signal A (Trig Pulser), which is a burst signal corresponding to the timing pulse for the ultrasonic wave output. The pulser/receiver 16 which has received the timing pulse signal A generates a given driving electric signal and supplies the driving electric signal to the transducer 12. The transducer 12 transforms the driving electric signal into an ultrasonic signal so as to emit the ultrasonic signal to the cell 20. The emitted ultrasonic signal propagates through the cell 20, is scattered while driving the fine particles 15, and returns toward the transducer 12 in a form of an ultrasonic scattered wave. The transducer 12 transforms, into an electric signal, the ultrasonic scattered wave which has propagated, and supplies the electric signal to the pulser/receiver 16.

Meanwhile, the arbitrary waveform generator 17 causes a second trigger out (Trigger out(2)) to supply, to the digital delay 18, a timing pulse signal B (Trig Digtizer), which is a burst signal corresponding to the timing pulse for the digitizer 19. Note here that the timing pulse signal B is in sync with the timing pulse signal A in accordance with a given rule. In FIG. 7, one timing pulse signal B is outputted every n timing pulse signals A. Note here that n represents a natural number. The pulser/receiver 16 causes a timing of Trig Digitizer of the digital delay 18 to delay Trig Pulser by a given time, and thereafter causes the digitizer 19 to record an electrically transduced scatter signal, which is a signal indicative of the scattered wave and outputted by the pulser/receiver 16.

The ultrasonic particle size measurement device 11 includes an ultrasonic fine particle velocity calculating section 13 and a particle size calculating section 14. The ultrasonic fine particle velocity calculating section 13 calculates the ultrasonic fine particle velocity by correcting, in accordance with the signal indicative of the scattered wave and recorded in the digitizer 19, a component based on attenuation of ultrasonic energy heading from the transducer 12 to the fine particles 15. The particle size calculating section 14 calculates a particle size of the fine particles 15 in accordance with the ultrasonic fine particle velocity calculated by the ultrasonic fine particle velocity calculating section 13.

(a) of FIG. 8 is a view schematically illustrating an arrangement of a conventional ultrasonic particle size measurement device 90. (b) of FIG. 8 is a timing chart showing a timing at which the pulser/receiver 16 which is provided in the ultrasonic particle size measurement device 90 supplies a driving signal to the transducer 12. (c) of FIG. 8 is a timing chart showing a timing at which a scatter signal electrically transduced by the digitizer 19 which is provided in the ultrasonic particle size measurement device 90 is recorded. 1/PRF shown in each of (a) and (b) of FIG. 8 is an interval between bursts (Burst Period) which interval shows a timing. In FIG. 8, emission of an ultrasonic wave and recording of a scattered wave are in a one-to-one correspondence.

A comparison between (a) an arrangement (setup) of the ultrasonic particle size measurement device 1 illustrated in FIG. 7 and in accordance with the active mode dynamic ultrasound scattering method of Embodiment 2 and (b) an arrangement of the ultrasonic particle size measurement device 90 illustrated in FIG. 8 and in accordance with the conventional passive mode dynamic ultrasound scattering method shows the following points of difference. Specifically, the arrangement of the ultrasonic particle size measurement device 1 and the arrangement of the ultrasonic particle size measurement device 90 differ in (i) intensity of an ultrasonic wave emitted to a fine particle, (ii) that the ultrasonic particle size measurement device 1 includes the ultrasonic fine particle velocity calculating section 13 and the particle size calculating section 14 each having a special function described below, and (iii) that emission of an ultrasonic wave and recording of a scattered wave influenced by a fine particle differ in number.

Examples of a typical setup of Embodiment 2 include a Z-direction setup in which the transducer 12 is provided so that ultrasonic energy is applied in a direction identical to a sedimentation direction and a Y-direction setup in which the transducer 12 is provided so that ultrasonic energy is applied perpendicularly to the sedimentation direction. In Embodiment 2, the latter Y-direction setup is used. Note, however, that the present invention is not limited to this. That is, use of the Z-direction setup also makes it possible to obtain a similar effect by making ultrasonic energy much greater than gravitational energy.

In Embodiment 2, in order that ultrasonic propagation attenuation in air and a loss in intensity of the ultrasonic wave which loss is caused by reflection of part of the ultrasonic wave at a boundary surface between the cell 20 and the solvent in the cell 20 less occur, the transducer 12 for outputting an ultrasonic wave and the cell 20 are provided in water for acoustic matching which water is contained in the water tank 21, and a setup in a back scattering mode in which a scattered wave is received by a transducer identical to a transducer for applying ultrasonic energy is used.

Note, however, that the present invention is not limited to the above. A scattered wave can be received by a transducer different from the transducer for applying ultrasonic energy. In this case, a scattering angle is considered. Further, as is widely used also in nondestructive testing, by thinly applying a contact medium for acoustic matching to a sensor (the transducer 12) so as to bring the transducer 12 into contact with the cell 20 so that no air space is provided between the cell 20 and the transducer 12, it is possible to carry out an experiment without using the water tank 21 in which the water for acoustic matching is contained.

In order that ultrasonic energy is transmitted, a commercially-available ultrasonic pulser (the pulser/receiver 16) is used to output a negative spike wave signal, and the transducer 12 transforms an electric signal to a mechanical signal (ultrasonic signal) and transmits an ultrasonic wave to the cell 20. The ultrasonic wave is scattered by the fine particles 15 in the cell 20, an ultrasonic scattered wave signal is transformed into an electric signal by the transducer 12, and the electric signal is recorded in the digitizer 19, which is at a high speed, after being amplified by an amplifier provided in the pulser/receiver 16.

(Ultrasonic Particle Size Measuring Method in Accordance with Embodiment 2)

Such a basic setup of Embodiment 2 as described earlier is similar to the conventional arrangement illustrated in FIG. 8. Note, however, that according to Embodiment 2, an ultrasonic wave applying method is devised so that greater pulse energy is applied to a sample obtained by dispersing fine particles into a liquid. As described earlier, (b) and (c) of FIG. 7 show the respective timing charts of Embodiment 2, and (b) and (c) of FIG. 8 show the respective conventional timing charts. Unlike conventional timing control, an arbitrary waveform generator 7 (see FIG. 7) of Embodiment 2 supplies a burst trigger (Trig Pulser illustrated in FIG. 7), which is larger in number of times of application of ultrasonic energy per unit time than Trig Pulser of the conventional method of FIG. 8, only to the pulser/receiver 16 so as to apply ultrasonic energy to the fine particles 15, which is the sample, at a shorter time interval than a recording system to the digitizer 19. That is, in FIG. 8, which shows a conventional example, a timing at which to emit an ultrasonic wave to a sample and a timing at which to record a scattered wave are in a one-to-one correspondence, whereas in FIG. 1 of Embodiment 2, a ratio between a timing at which to emit an ultrasonic wave to a sample and a timing at which to record a scattered wave (the number of times of reception of a scattered wave) is n (n is a natural number indicative of the number of times of emission (the number of times of application) of an ultrasonic wave): 1. With the arrangement, while memory consumption by the digitizer 19, which is the recording system, is reduced and scattered wave data having sufficient time resolving power energy is allowed to be recorded in the digitizer 19, energy to be applied to a fine particle by an ultrasonic wave can be controlled independently of recording of the scattered wave in the digitizer 19 without the need to make ultrasonic energy extremely large. That is, an increase in number of times of application n allows an increase in energy to be applied to a fine particle by an ultrasonic wave. It is a matter of course that an increase in energy of an ultrasonic wave to be emitted at one time makes it possible to obtain an effect of Embodiment 2 even in a case where n=1.

Note that as an analysis method for calculating a particle size, a correlation function method and a lock-in phase method which are similar to the conventional correlation function method and the conventional lock-in phase method, respectively, can be used. In a case where evaluation is carried out by the correlation function method, substitution of numerical values into $\pi$, $\eta$, a, and E, respectively, in the following Equation (13) makes it possible to obtain (i) an ultrasonic fine particle velocity <Vy> induced in a fine particle to which ultrasonic energy has been applied and (ii) a standard deviation $<\delta V_y^2>^{1/2}$ of the ultrasonic fine particle velocity <Vy>. The particle size is found based on Equation (13) expressing a balance between (a) a force based on ultrasonic energy heading in a direction intersecting a direction in which the fine particle sediments and (b) a frictional force exerted on the fine particle.

[Math. 14]

$$6\pi\eta a \langle V_y \rangle = E \qquad \text{Equation (13)}$$

where a is a hydrodynamic radius, and E is ultrasonic energy.

The ultrasonic energy E, which can be empirically found, can be calculated in advance. This is because there are various theories as to, for example, a suspension in which a scatterer is present. The theory of Hasegawa-Yoshioka (Hasegawa, T., 1969, Acoustic-Radiation Force on a Solid Elastic Sphere, J. Acoust. Soc. Am. 46, 58, 1139) includes a theory in which a scattering function of a rigid particle is taken into consideration for acoustic streaming represented by the following Equation (14).

[Math. 15]

$$E = \pi a^2 \frac{I_0}{c} Y_p \qquad \text{Equation (14)}$$

where $I_0$ is an incident intensity, c is a sound velocity of a dispersion medium, and Yp is a an acoustic radiation function.

(a) of FIG. 9 shows a graph indicating a relationship between (a) an ultrasonic fine particle velocity Vy calculated by the ultrasonic fine particle velocity calculating section 13 provided in the ultrasonic particle size measurement device 11 in accordance with Embodiment 2 and (b) a sample location Y. (b) of FIG. 9 is a view for explaining attenuation of ultrasonic energy heading in a Y direction (e.g., a direction in which the fine particles 15 are present) from the transducer 12 provided in the ultrasonic particle size measurement device 11.

As shown in (a) of FIG. 9, the ultrasonic fine particle velocity $<V_y>$ of a fine particle 15 which ultrasonic fine particle velocity is obtained by the ultrasonic fine particle velocity calculating section 13 in accordance with a scattered wave of the fine particle 15 depends on the sample location Y of the fine particle in a direction in which ultrasonic energy is applied. (a) of FIG. 9 shows a result of measurement carried out with respect to the fine particle 15 having a particle size of 15 μm and a concentration of 1%. Such a phenomenon in which the ultrasonic fine particle velocity $<V_y>$ is induced in the fine particle 15 is a cumulative effect yielded by an emitted ultrasonic wave. Thus, the ultrasonic fine particle velocity $<V_y>$ gradually increases from the sample which is located closer to a wall of the cell 20 which wall is adjacent to the transducer 12, and thereafter reaches a maximum and decreases (a curve C1). Such a decrease is due to attenuation of an intensity of ultrasonic energy incident on the cell 20. Thus, the attenuation is corrected first so that the ultrasonic fine particle velocity is calculated.

FIG. 10 shows a graph for explaining an aspect in which attenuation of the ultrasonic energy is corrected. Specifically, an entirety of the ultrasonic fine particle velocity $<V_y>$, which is measurement data, is divided as below by an attenuation function in which an attenuated part of the curve C1 is replaced with an exponential function.

$$<V_y>/\exp(-\alpha ct/2)$$

Then, as shown in the curve C2 of FIG. 10, it can be confirmed that the ultrasonic fine particle velocity $<V_y>$ of the fine particle 5 is made constant. As a coefficient α of the exponential function exp, a coefficient obtained from a constant velocity can be empirically found. Note, however, the coefficient α can also be predicted from a scattering function theory.

Hereinafter, $<V_y>/\exp(-\alpha ct/2)$ is simply referred to as the ultrasonic fine particle velocity $<V_y>$.

FIG. 11 shows a graph indicating, for each particle size of the fine particle 15, a relationship between (a) the ultrasonic fine particle velocity $<V_y>$ and (b) a concentration c of the fine particle 15 in a case where irradiation ultrasonic energy is made constant. FIG. 11 shows concentration dependence on the ultrasonic fine particle velocity $<V_y>$. FIG. 11 also shows a result of measurement with respect to the fine particle 15 having various particle sizes in a range of 5 μm to 30 μm. As shown in FIG. 11, the ultrasonic fine particle velocity $<V_y>$ is substantially linear with respect to the concentration c in a low concentration region. Meanwhile, it is revealed that in a high concentration region, the ultrasonic fine particle velocity $<V_y>$ converges at a constant value while deviating from a linear straight line.

The particle size of the fine particle 15 needs to be analyzed in a low concentration region in which the ultrasonic fine particle velocity $<V_y>$ is linear with respect to the concentration c. Thus, in a case where the particle size is great, a problem such that measurement data deviates from the linear straight line on the high concentration side is suggested. Note, however, that such a phenomenon of deviation of the measurement data from the linear straight line is a phenomenon that is already well known as resonance scattering also in a conventional ultrasonic spectroscopy method. It is known that also according to the ultrasonic spectroscopy method, use of a transducer having a lower frequency makes it possible to solve the above problem in a case where a fine particle having a great particle size may cause resonance scattering. Thus, in a case where a fine particle has a great particle size, as in the case of the ultrasonic spectroscopy method, Embodiment 2 makes it possible to solve the above problem by use of a transducer capable of transmitting an ultrasonic wave having a lower frequency.

Further, since an influence of a concentration can also be analyzed in accordance with an ultrasonic attenuation rate as described later, the active mode dynamic ultrasound scattering method in accordance with Embodiment 2 can also be utilized to a several ten percent concentration region.

FIG. 12 shows a graph indicating a relationship between (a) a variable for the ultrasonic fine particle velocity $<V_y>$ and (b) a particle size d of the fine particle 15. In a case where an experiment is carried out by use of the fine particle 15 whose concentration is low, an inclination of concentration dependence, i.e., an inclination of the linear straight line shown in FIG. 11 is found. An intercept of the linear straight line obtained by plotting the ultrasonic fine particle velocity $<V_y>$ and the concentration c of the fine particle 15 shows that the concentration c is zero, i.e., a stream velocity, which is a velocity of a flow of a solvent in which no fine particle 15 is present. The inclination of the linear straight line shows an increment of the ultrasonic fine particle velocity $<V_y>$ due to fine particle scattering in response to a minor change in concentration. Thus, it is possible to extract a property in accordance with the particle size of the fine particle from the following variable (this corresponds to the inclination of the linear straight line) obtained by subtracting a value of the intercept $<V_y>_0$ from the ultrasonic fine particle velocity $<V_y>$ and dividing, by the concentration c, a result obtained by subtracting the value of the intercept $<V_y>_0$ from the ultrasonic fine particle velocity $<V_y>$.

FIG. 12 shows a graph obtained by plotting a variable $(<V_y>-<V_y>_0)/c$ and the particle size d. It is observed in the graph of FIG. 12 that in an experiment in which ultrasonic energy has a frequency of 30 MHz, dependence of the variable on the particle size d (i) is constant in a case where the particle size d is not more than 10 μm, (ii) rises in a case where the particle size d is more than 10 μm and less than 30 μm, and (iii) gently inclines in a case where the particle size d increases to not less than 30 μm. Note that a solid line illustrated in FIG. 12 shows a theoretical prediction curve. Note also that an effect of a frequency distribution obtained by calibrating a frequency distribution of an actual ultrasonic transducer by use of a hydrophone (underwater ultrasonic sensor) is taken into consideration for calculation of an acoustic radiation function Yp of a theory.

(a) of FIG. 13 shows a graph indicating a frequency characteristic of the transducer 12. (b) of FIG. 13 shows graphs each indicating particle size dependence of the acoustic radiation function Yp (function form of acoustic radiation power) in accordance with Embodiment 2. (a) of FIG. 13 shows frequency dependence of an ultrasonic acoustic pressure obtained by calibrating, by use of a hydrophone, the transducer 12, which is used in Embodiment 2, has a frequency of 30 MHz, and is of a composite type. Since an ultrasonic pulse (ultrasonic energy) emitted from the transducer 12 contains various frequency components, motion of the fine particle 15 which is driven by the ultrasonic pulse is also influenced by the ultrasonic acoustic pressure of the various frequency components. Thus, an average of the frequency components is calculated in advance by use of the acoustic radiation function Yp of Equation (2).

(b) of FIG. 13 shows (i) a curve C3 indicative of particle size dependence of the acoustic radiation function Yp corresponding to a frequency of 30 MHz of ultrasonic energy and (ii) a curve C4 indicative of particle size dependence of the acoustic radiation function Yp obtained by averaging, in view of an amplitude spectrum, used in the present experiment, of ultrasonic energy having a frequency of 30 MHz, various acoustic radiation functions Yp corresponding to respective various frequency components in the amplitude spectrum. Note, however, that such an averaging operation is unnecessary in a case where the transducer 12 which includes a narrow-band sensor having a relatively narrow frequency distribution is used.

A final average particle size d is calculated in accordance with a value of a hydrodynamic radius a that causes a value obtained by subtracting 1 from a result obtained by dividing the right-hand side of Equation (13) by the left-hand side of Equation (13) to be zero. FIG. 14 shows a relationship between (a) a particle size $d_{Active}$ obtained by such an active mode dynamic ultrasound scattering method of Embodiment 2 and (b) a particle size $d_{SEM}$ measured by use of a scanning electron microscope (SEM). As shown in FIG. 14, a value of the particle size $d_{Active}$ and a value of the particle size $d_{SEM}$ substantially match each other in a region of a particle size of not less than a dozen or so μm. Thus, it can be confirmed by the active mode dynamic ultrasound scattering method of Embodiment 2 that the particle size of the fine particle 15 is correctly calculated at not less than a dozen or so μm.

Note that no particle size of a small fine particle having a particle size of less than a dozen or so μm is plotted in FIG. 14. This is because of the following reason. Specifically, in the present experiment, the transducer used produces a low ultrasonic energy output, and ultrasonic energy applied is insufficient to move a small fine particle, having a particle size of less than a dozen or so μm, by inducing an ultrasonic fine particle velocity in the small fine particle. Thus, the ultrasonic fine particle velocity is substantially zero, so that the particle size cannot be calculated. Note, however, that by using a transducer that produces a higher output and applying greater ultrasonic energy to a fine particle, it is possible to apply the active mode dynamic ultrasound scattering method of Embodiment 2 also to a small fine particle, having a particle size of less than a dozen or so μm, by inducing an ultrasonic fine particle velocity in the small fine particle.

Embodiment 2, in which the experiment is carried out under an echo setup as a simple and easy example, shows an example in which one transducer 2 carries out both a function of transmitting ultrasonic energy and a function of receiving an ultrasonic scattered wave. Note, however, that the present invention is not limited to this. The active mode dynamic ultrasound scattering method of Embodiment 2 is also applicable to a case where a transducer for transmitting ultrasonic energy and a transducer for receiving a scattered wave are separately provided or provided at any angle. It is easy to obtain measurement data by (i) causing a transducer for transmission to transmit powerful ultrasonic energy and (ii) using a conventional sensor as a transducer for reception to cause the conventional sensor to receive a scattered wave.

Actually, the conventional passive mode dynamic ultrasound scattering method has already achieved measurement of a particle size of an extremely small fine particle having a particle size of 0.1 μm.

According to the measurement data shown in Embodiment 2, a particle size of a fine particle and a concentration of a fine particle are limited in scope of application. Note, however, that the scope of application can be less limited by applying greater ultrasonic energy to a fine particle as described earlier.

A particle size of a fine particle can also be found by the conventional ultrasonic spectroscopy method. Note, however, the conventional ultrasonic spectroscopy method makes it extremely difficult to observe weakly aggregated fine particles and an aggregate of isolate fine particles. According to the ultrasonic spectroscopy method in which a wavelength of an ultrasonic wave is much longer than a particle size of a fine particle, since an aggregate of fine particles is seen as a single large particle, it is theoretically possible to sense aggregated fine particles by use of a low-frequency ultrasonic wave having a long wavelength. Note, however, that a signal based on the low-frequency ultrasonic wave is extremely weak. This makes it difficult to see a fine particle by use of a long wavelength. Further, use of a transducer whose frequency is so low as to see an aggregate of fine particles as a single large particle causes a problem such that a water tank in which to contain the transducer has a massive size.

FIG. 15 shows graphs for explaining a difference in measurement time between the ultrasonic particle size measuring method in accordance with Embodiment 2 and a conventional ultrasonic particle size measuring method. FIG. 15 shows a difference in measurement data of a polydivinylbenzene (PDVB) particle having a particle size of 5 μm, the measurement data having been obtained by each of the conventional passive mode dynamic ultrasound scattering method and the active mode dynamic ultrasound scattering method in accordance with an embodiment.

A curve C5 indicative of a correlation function related to the measurement data obtained by the passive mode dynamic ultrasound scattering method is an example of measuring a sedimentation velocity of a fine particle from a Z direction (sedimentation direction) while being careful not to apply, to the fine particle, a load derived from ultrasonic energy. The curve C5 indicative of the correlation function is attenuated from 1 to a negative value and then has a minimum value. Thereafter, the curve C5 fluctuates several times and then is relaxed at a value near 0 (zero). The sedimentation velocity of the fine particle is obtained from the initial negative minimum value and converted into a particle size. A time required for this measurement can be read from a horizontal axis of FIG. 15. The curve C5 reveals that according to the conventional passive mode dynamic ultrasound scattering method, the measurement is carried out for a long time that is more than $10^3$ seconds=1000 seconds.

Meanwhile, C6 is a curve indicative of a correlation function obtained by carrying out an experiment by the active mode dynamic ultrasound scattering method under a setup in which ultrasonic energy is applied in a direction (horizontal direction) perpendicular to the sedimentation direction. Thus, an influence of gravity on ultrasonic energy can be originally substantially ignored. Note, however, that since a direction in which ultrasonic energy is applied is orthogonal to the sedimentation direction under the above setup, the influence of gravity can be eliminated. As described earlier, according to the active mode dynamic ultrasound scattering method, an ultrasonic fine particle velocity to be induced in a fine particle is converted into a particle size by purely solving a balance between (a) ultrasonic energy applied to the fine particle in the horizontal direction and (b) a frictional resistance exerted on the fine particle to which the ultrasonic energy is being applied (Equation (1) of balance). The curve C6 reveals that a time required for this measurement is approximately $10^{-1}$ seconds=0.1 seconds. It can be understood from FIG. 15 that the measurement time in the active mode dynamic ultrasound scattering method is made shorter by approximately 4 digits than the measurement time of $10^3$ seconds in the passive mode dynamic ultrasound scattering method.

As described earlier, in a case where ultrasonic energy is actively applied to a sample containing a fine particle that is difficult to move or cannot move, such as a sample containing a concentrated fine particle or a sample containing a highly viscous fine particle, a state of the fine particle can be determined in accordance with a response from the fine particle to which ultrasonic energy has been applied.

The active mode dynamic ultrasound scattering method in accordance with Embodiment 2 shows that a correlation function method and a lock-in phase method which are similar to the conventional correlation function method and the conventional lock-in phase method, respectively, can be used as an analysis method for calculating a particle size. Note, however, that motion and a particle size of a fine particle can be analyzed with higher accuracy, at a higher S/N ratio, and in a shorter time in a case where a frequency domain complex correlation function method described in Embodiment 1 is used as the analysis method.

It is possible to arrange an ultrasonic measurement apparatus including: the ultrasonic particle size measurement device 11 in accordance with Embodiment 2; and the ultrasonic particle size measurement device 1 in accordance with Embodiment 1.

(Different Aspect of Present Invention)

In order to attain the first object, an ultrasonic particle size measurement device in accordance with an embodiment of the present invention includes: an ultrasonic wave receiver for (i) receiving an ultrasonic pulse scattered after being emitted to a fine particle sedimenting in a liquid and (ii) generating a first scattering amplitude Ψ (t,T) based on a propagation time t of the ultrasonic pulse and an observation time T with respect to motion of the fine particle; and a particle size calculating section for (i) generating a second scattering amplitude Ψ (f,T) obtained by subjecting the first scattering amplitude Ψ (t,T) to a Fourier transform in a direction of the propagation time t, (ii) calculating an amplitude r (f,T) and a phase θ (f,T) in accordance with a real part and an imaginary part, respectively, of the second scattering amplitude Ψ (f,T), and (iii) calculating a particle size of the fine particle in accordance with the amplitude r (f,T) and the phase θ (f,T).

With the feature, since an amplitude r (f,T) and a phase θ (f,T) are calculated in accordance with a real part and an imaginary part, respectively, of a second scattering amplitude Ψ (f,T) obtained by subjecting the first scattering amplitude Ψ (t,T) to a Fourier transform in a direction of the propagation time t, and a particle size of the fine particle is calculated in accordance with the amplitude r (f,T) and the phase θ (f,T), a particle size of a fine particle that is in sedimentation motion can be measured with extremely high accuracy.

The ultrasonic particle size measurement device in accordance with an embodiment of the present invention is preferably arranged such that the particle size calculating section calculates a motion velocity of the fine particle in accordance with the amplitude r (f,T) and the phase θ (f,T) and calculates the particle size in accordance with the motion velocity.

The arrangement makes it possible to simplify calculation of a particle size of a fine particle.

The ultrasonic particle size measurement device in accordance with an embodiment of the present invention is preferably arranged such that the particle size calculating section generates a complex correlation function in accordance with the amplitude r (f,T) and the phase θ (f,T) and calculates the particle size in accordance with the complex correlation function.

With the arrangement, a particle size of a fine particle that is in sedimentation motion can be measured with extremely high accuracy by use of the complex correlation function which is based on the amplitude r (f,T) and the phase θ (f,T).

The ultrasonic particle size measurement device in accordance with an embodiment of the present invention is preferably arranged such that the particle size calculating section rewrites the second scattering amplitude Ψ (f,T) by use of the amplitude r (f,T) and the phase θ (f,T), generates a complex correlation function by use of the second scattering amplitude Ψ (f,T) and a conjugate form of the second scattering amplitude Ψ (f,T), and calculates the particle size in accordance with the complex correlation function.

With the arrangement, a particle size of a fine particle that is in sedimentation motion can be measured with extremely high accuracy by generating the complex correlation function by use of the conjugate form of the second scattering amplitude Ψ (f,T).

The ultrasonic particle size measurement device in accordance with an embodiment of the present invention is preferably arranged such that the particle size calculating section calculates the particle size of the fine particle in accordance with the second scattering amplitude represented by the following equation:

[Math. 7]

$$\psi(f, T) = r(f, T)\exp\left[i\tan^{-1}\frac{\sin\theta(f, T) - \langle\sin\theta\rangle_T(f)}{\cos\theta(f, T) - \langle\cos\theta\rangle_T(f)}\right] \quad \text{Equation (7)}$$

With the arrangement, a particle size of a fine particle that is in sedimentation motion can be measured with extremely high accuracy in accordance with the real part and the imaginary part of the second scattering amplitude Ψ (f,T).

The ultrasonic particle size measurement device in accordance with an embodiment of the present invention is preferably arranged such that: the particle size calculating section generates the complex correlation function represented by the following equation:

[Math. 8]

$$g^{(1)}(f, \tau) = \frac{\langle\psi(f, T)\psi^*(f, T+\tau)\rangle_T}{\langle\psi(f, T)\psi^*(f, T)\rangle_T}; \quad \text{Equation (8)}$$

the particle size calculating section calculates the particle size in accordance with the complex correlation function.

With the arrangement, a particle size of a fine particle that is in sedimentation motion or Brownian motion can be measured with extremely high accuracy by use of the complex correlation function which is based on the amplitude r (f,T) and the phase θ (f,T).

In order to attain the second object, an ultrasonic particle size measurement device in accordance with an embodiment of the present invention includes: an ultrasonic energy applicator for applying ultrasonic energy to a fine particle so as to induce an ultrasonic fine particle velocity in the fine particle; a scattered wave receiver for receiving a scattered wave scattered by the fine particle in which the ultrasonic fine particle velocity has been induced; an ultrasonic fine particle velocity calculating section for calculating the ultrasonic fine particle velocity in accordance with the scattered wave received by the scattered wave receiver; and a particle size calculating section for calculating a particle size of the fine particle in accordance with the ultrasonic fine particle velocity calculated by the ultrasonic fine particle velocity calculating section.

With the feature, the particle size of the fine particle is calculated in accordance with the ultrasonic fine particle velocity calculated in accordance with the scattered wave scattered by the fine particle in which the ultrasonic fine particle velocity has been induced by application of ultrasonic energy to the fine particle is calculated. Thus, the particle size of the fine particle can be measured at a favorable SN ratio and in a short time.

The ultrasonic particle size measurement device in accordance with an embodiment of the present invention is preferably arranged such that a ratio between (a) the number of times of application of the ultrasonic energy by the ultrasonic energy applicator and (b) the number of times of reception of the scattered wave by the scattered wave receiver in accordance with the number of times of the application is n (n is a natural number): 1.

With the arrangement, energy to be applied to a fine particle by an ultrasonic wave can be controlled independently of recording of the scattered wave. Further, an increase in n allows an increase in energy to be applied to a fine particle by an ultrasonic wave.

The ultrasonic particle size measurement device in accordance with an embodiment of the present invention is preferably arranged such that the ultrasonic fine particle velocity calculating section calculates the ultrasonic fine particle velocity by correcting a component based on attenuation of the ultrasonic energy applied to the fine particle by the ultrasonic energy applicator.

With the arrangement, it is possible to reduce an error in calculation of the ultrasonic fine particle velocity which is based on attenuation of the ultrasonic energy applied to the fine particle by the ultrasonic energy applicator.

The ultrasonic particle size measurement device in accordance with an embodiment of the present invention is preferably arranged such that the particle size calculating section calculates the particle size of the fine particle in accordance with a concentration of the fine particle and the ultrasonic fine particle velocity.

With the arrangement, accuracy with which to measure a particle size can be improved based on concentration dependence of the ultrasonic fine particle velocity.

The ultrasonic particle size measurement device in accordance with an embodiment of the present invention is preferably arranged such that the fine particle is a sedimenting fine particle.

With the arrangement, a particle size of a fine particle having a particle size of more than 100 nm can be measured at a favorable SN ratio and in a short time.

The ultrasonic particle size measurement device in accordance with an embodiment of the present invention is preferably arranged such that the ultrasonic energy applicator applies the ultrasonic energy in a direction intersecting a direction in which the fine particle sediments.

With the arrangement, a particle size of a fine particle can be precisely measured while an influence of gravity is eliminated.

An ultrasonic measurement apparatus in accordance with an embodiment of the present invention includes: a first ultrasonic particle size measurement device in accordance with an embodiment of the present invention; and a second ultrasonic particle size measurement device in accordance with an embodiment of the present invention.

The present invention is not limited to the embodiments, but can be altered by a skilled person in the art within the scope of the claims. An embodiment derived from a proper combination of technical means each disclosed in a different embodiment is also encompassed in the technical scope of the present invention.

INDUSTRIAL APPLICABILITY

The present invention provides an ultrasonic particle size measurement device for measuring, by use of an ultrasonic pulse, a particle size of fine particles dispersed into a liquid. The ultrasonic particle size measurement device of the present invention is used to measure a particle size of a fine particle constituting, for example, ink, cosmetics, paint, slurry for ceramics, or slurry for powder metallurgy. The ultrasonic particle size measurement device of the present invention can also be used in the field of, for example, ink or cosmetics constituted by a fine particle.

REFERENCE SIGNS LIST

1 Ultrasonic particle size measurement device
2 Transducer (ultrasonic wave transmitter-receiver)
3 Particle size calculating section
4 Cell
5 Fine particle
11 Ultrasonic particle size measurement device
12 Transducer (ultrasonic energy applicator, scattered wave receiver)
13 Ultrasonic fine particle velocity calculating section
14 Particle size calculating section
15 Fine particle

The invention claimed is:
1. An ultrasonic particle size measurement device comprising:
an ultrasonic wave receiver for (i) receiving an ultrasonic pulse scattered after being emitted to a fine particle sedimenting in a liquid and (ii) generating a first scattering amplitude Ψ (t,T) based on a propagation time t of the ultrasonic pulse and an observation time T with respect to motion of the fine particle; and
a particle size calculating section for (i) generating a second scattering amplitude Ψ (f,T) obtained by subjecting the first scattering amplitude Ψ (t,T) to a Fourier transform in a direction of the propagation time t, (ii) calculating an amplitude r (f,T) and a phase θ (f,T) in accordance with a real part and an imaginary part, respectively, of the second scattering amplitude Ψ (f,T), and (iii) calculating a particle size of the fine particle in accordance with the amplitude r (f,T) and the phase θ (f,T).
2. The ultrasonic particle size measurement device as set forth in claim 1, wherein the particle size calculating section calculates a motion velocity of the fine particle in accor- dance with the amplitude r (f,T) and the phase θ (f,T) and calculates the particle size in accordance with the motion velocity.

3. The ultrasonic particle size measurement device as set forth in claim 1, wherein the particle size calculating section generates a complex correlation function in accordance with the amplitude r (f,T) and the phase θ (f,T) and calculates the particle size in accordance with the complex correlation function.

4. The ultrasonic particle size measurement device as set forth in claim 3, wherein:

the particle size calculating section generates the complex correlation function represented by the following equation:

[Math. 2]

$$g^{(1)}(f,\tau) = \frac{\langle \psi(f,T)\psi^*(f,T+\tau)\rangle_T}{\langle \psi(f,T)\psi^*(f,T)\rangle_T};$$

and the particle size calculating section calculates the particle size in accordance with the complex correlation function.

5. The ultrasonic particle size measurement device as set forth in claim 1, wherein the particle size calculating section rewrites the second scattering amplitude Ψ (f,T) by use of the amplitude r (f,T) and the phase (f,T), generates a complex correlation function by use of the second scattering amplitude Ψ (f,T) and a conjugate form of the second scattering amplitude Ψ (f,T), and calculates the particle size in accordance with the complex correlation function.

6. The ultrasonic particle size measurement device as set forth in claim 1, wherein the particle size calculating section calculates the particle size of the fine particle in accordance with the second scattering amplitude represented by the following equation:

[Math. 1]

$$\psi(f,T) = r(f,T)\exp\left[i\tan^{-1}\frac{\sin\theta(f,T) - \langle\sin\theta\rangle_T(f)}{\cos\theta(f,T) - \langle\cos\theta\rangle_T(f)}\right].$$

7. An ultrasonic measurement apparatus comprising:
an ultrasonic particle size measurement device recited in claim 1; and
an ultrasonic particle size measurement device comprising:
an ultrasonic energy applicator for applying ultrasonic energy to a fine particle so as to induce an ultrasonic fine particle velocity in the fine particle;
a scattered wave receiver for receiving a scattered wave scattered by the fine particle in which the ultrasonic fine particle velocity has been induced;
an ultrasonic fine particle velocity calculating section for calculating the ultrasonic fine particle velocity in accordance with the scattered wave received by the scattered wave receiver; and
a particle size calculating section for calculating a particle size of the fine particle in accordance with the ultrasonic fine particle velocity calculated by the ultrasonic fine particle velocity calculating section.

8. An ultrasonic particle size measurement device comprising:
an ultrasonic energy applicator for applying ultrasonic energy to a sample in which a fine particle is dispersed in a solution so as to induce an ultrasonic fine particle velocity in the fine particle, the ultrasonic fine particle velocity indicating a velocity of the fine particle induced by application of ultrasonic energy;
a scattered wave receiver for receiving a scattered wave scattered by the fine particle in which the ultrasonic fine particle velocity has been induced;
an ultrasonic fine particle velocity calculating section for calculating the ultrasonic fine particle velocity in accordance with the scattered wave received by the scattered wave receiver; and
a particle size calculating section for calculating a particle size of the fine particle in accordance with the ultrasonic fine particle velocity calculated by the ultrasonic fine particle velocity calculating section.

9. The ultrasonic particle size measurement device as set forth in claim 8, wherein a ratio between (a) the number of times of application of the ultrasonic energy by the ultrasonic energy applicator and (b) the number of times of reception of the scattered wave by the scattered wave receiver in accordance with the number of times of the application is n (n is a natural number): 1.

10. The ultrasonic particle size measurement device as set forth in claim 8, wherein the ultrasonic fine particle velocity calculating section calculates the ultrasonic fine particle velocity by correcting a component based on attenuation of the ultrasonic energy applied to the fine particle by the ultrasonic energy applicator.

11. The ultrasonic particle size measurement device as set forth in claim 8, wherein the particle size calculating section calculates the particle size of the fine particle in accordance with a concentration of the fine particle and the ultrasonic fine particle velocity.

12. The ultrasonic particle size measurement device as set forth in claim 8, wherein the fine particle is a sedimenting fine particle.

13. The ultrasonic particle size measurement device as set forth in claim 8, wherein the ultrasonic energy applicator applies the ultrasonic energy in a direction intersecting a direction in which the fine particle sediments.

\* \* \* \* \*